US011059880B2

(12) United States Patent
Kuhns et al.

(10) Patent No.: US 11,059,880 B2
(45) Date of Patent: Jul. 13, 2021

(54) REDIRECTED CELLS WITH MHC CHIMERIC RECEPTORS AND METHODS OF USE IN IMMUNOTHERAPY

(71) Applicants: THE ARIZONA BOARD OF REGENTS ON BEHALF OF THE UNIVERSITY OF ARIZONA, Tucson, AZ (US); JOSLIN DIABETES CENTER, INC., Boston, MA (US)

(72) Inventors: Michael S. Kuhns, Tucson, AZ (US); Thomas Serwold, Boston, MA (US)

(73) Assignees: ARIZONA BOARD OF REGENTS ON BEHALF OF THE UNIVERSITY OF ARIZONA, Tucson, AZ (US); JOSLIN DIABETES, CENTER, INC., Boston, MA (US)

( * ) Notice: Subject to any disclaimer, the term of this patent is extended or adjusted under 35 U.S.C. 154(b) by 177 days.

(21) Appl. No.: 15/738,467

(22) PCT Filed: Jun. 29, 2016

(86) PCT No.: PCT/US2016/040177
§ 371 (c)(1),
(2) Date: Dec. 20, 2017

(87) PCT Pub. No.: WO2017/004252
PCT Pub. Date: Jan. 5, 2017

(65) Prior Publication Data
US 2018/0179260 A1    Jun. 28, 2018

Related U.S. Application Data

(60) Provisional application No. 62/186,865, filed on Jun. 30, 2015.

(51) Int. Cl.
| C07K 14/74 | (2006.01) |
| C07K 14/725 | (2006.01) |
| C07K 14/705 | (2006.01) |
| A61K 35/17 | (2015.01) |
| C12N 5/0783 | (2010.01) |
| C12N 9/12 | (2006.01) |

(52) U.S. Cl.
CPC ........ *C07K 14/70539* (2013.01); *A61K 35/17* (2013.01); *C07K 14/705* (2013.01); *C07K 14/7051* (2013.01); *C12N 5/0636* (2013.01); *C12N 9/12* (2013.01); *C12Y 207/10002* (2013.01); *C07K 2319/02* (2013.01); *C07K 2319/03* (2013.01); *C07K 2319/74* (2013.01)

(58) Field of Classification Search
None
See application file for complete search history.

(56) References Cited

U.S. PATENT DOCUMENTS

| 6,056,952 A | 5/2000 | Rosenberg |
| 6,268,411 B1 | 7/2001 | Schneck et al. |
| 6,319,494 B1 | 11/2001 | Capon et al. |
| 6,407,221 B1 | 6/2002 | Capon et al. |
| 6,410,319 B1 | 6/2002 | Raubitschek et al. |
| 7,741,465 B1 | 6/2010 | Eshhar |
| 7,871,817 B2 | 1/2011 | Voss et al. |
| 8,450,112 B2 | 5/2013 | Li et al. |
| 8,524,234 B2 | 9/2013 | Getts et al. |
| 8,906,383 B2 | 12/2014 | Peakman et al. |
| 2004/0258697 A1 | 12/2004 | Brumeanu et al. |
| 2013/0287748 A1 | 10/2013 | June et al. |
| 2014/0219975 A1 | 8/2014 | June et al. |
| 2017/0166622 A1* | 6/2017 | Baeuerle ................ C07K 16/40 |
| 2019/0345485 A1* | 11/2019 | Kisielow ............ C12N 15/1055 |

FOREIGN PATENT DOCUMENTS

| EP | 2659893 A2 | 2/2014 |
| WO | WO1992015322 A1 | 9/1992 |
| WO | WO1996025953 A1 | 8/1996 |
| WO | WO2002026833 A1 | 4/2002 |
| WO | WO2002072850 A1 | 9/2002 |
| WO | WO2005054292 A1 | 6/2005 |
| WO | WO2011101681 A2 | 8/2011 |
| WO | WO2014117121 A1 | 7/2014 |
| WO | WO2016070061 A1 | 5/2016 |

OTHER PUBLICATIONS

Brogdon et al., J Immunol 1998; 161:5472-5480. (Year: 1998).*
Backstrom et al. Immunity. Nov. 1996;5(5):437-47. (Year: 1996).*
Trowsdale et al. (Annu Rev Genomics Hum Genet. 2013;14:301-23). (Year: 2013).*
Lefranc et al. ("The T cell receptor FactsBook," p. ix, 3-397 (2001)) . (Year: 2001).*
Li et al., Front Immunol. Jul. 22, 2013;4:206. (Year: 2013).*
Liu et al., eLS. John Wiley & Sons, Ltd: Chichester. (2011) pp. 1-12. (Year: 2011).*
Macian, Nat Rev Immunol. Jun. 2005;5(6):472-84. (Year: 2005).*
Painter et al., Immunological Reviews, 2012, vol. 250: 144-157. (Year: 2012).*
Xu et al., JBC, 2006, vol. 281, No. 48, p. 36977-36984. (Year: 2006).*

(Continued)

*Primary Examiner* — Zachary S Skelding
(74) *Attorney, Agent, or Firm* — Nguyen Tarbet LLC

(57) ABSTRACT

Chimeric receptors featuring major histocompatibility molecules grafted onto T cell receptor molecules and surrogate co-receptors featuring cell surface receptor ligands fused with signaling molecule domains. The chimeric receptors can be used to redirect cells, altering their specificity. T cells expressing chimeric receptors may bind to ICRs of target T cells for which their chimeric receptors are specific. Surrogate co-receptors may be used to help enhance TCR-CD3 signaling as part of this modular receptor system. The chimeric receptors and surrogate coreceptors may be used to help eliminate autoreactive T cells or program T cells to desired effector functions.

10 Claims, 4 Drawing Sheets
(4 of 4 Drawing Sheet(s) Filed in Color)

Specification includes a Sequence Listing.

(56) References Cited

OTHER PUBLICATIONS

Yin et al., Proc Natl Acad Sci USA. Apr. 3, 2012;109(14):5405-10. (Year: 2012).*

Wucherpfennig et al., Cold Spring Harb Perspect Biol. Apr. 2010;2(4):a005140. (Year: 2010).*

Perez, S. et al. Selective immunotargeting of diabetogenic CD4 T cells by genetically redirected T cells- Immunology 2014, 143, 609-617.

Eshhar, Zelig, Adoptive cell therapy of autoimmune diseases employing genetically T regulatory cells with redirected antibody specificity, International Conference on Emerging Cell Therapies, Oct. 1-3, 2012. J Cell Sci Ther 2012, 3:7 http://dx.doi.org/10.4172/2157-7013.S1.004.

Casares, S. et al. Engineering and characterization of a murine MHC class II—immunoglobulin chimera expressing an immunodominant CD4 T viral epitope, Protein Eng. Nov. 1997;10(11):1295-301.

Mottez, E. et al. Cells expressing a major histocompatibility complex class I molecule with a single covalently bound peptide are highly immunogenic. J. Exp. Med. vol. 181 Feb. 1995 493-502.

Willemsen, RA. et al., T Cell Retargeting with MHC Class I-Restricted Antibodies: The CD28 Costimulatory Domain. Enhances Antigen-Specific Cytotoxicity and Cytokine ProductionI. J Immunol. Jun. 15, 2005;174(12):7853-8.

Dotti, Gianpietro, The Other Face of Chimeric Antigen Receptors, www.moleculartherapy.org vol. 22 No. 5 May 2014.

Bridgeman, John S. et al. The Optimal Antigen Response of Chimeric Antigen Receptors Harboring the CD3z Transmembrane Domain Is Dependent upon Incorporation of the Receptor into the Endogenous TCR/CD3 Complex. The Journal of Immunology, May 17, 2010.

Brien JD, Uhrlaub JL, Hirsch A, Wiley CA, Nikolich-Zugich J. Key role of T cell defects in age-related vulnerability to West Nile virus. J Exp Med. 2009;206(12):2735-45. Epub Nov. 11, 2009. doi: jem.20090222 [pii] 10.1084/jem.20090222. PubMed PMID: 19901080.

Casares, et al., Insights into the Pathogenesis of Type 1 Diabetes a Hint for Novel Immunospecific Therapies S, Current Molecular Medicine, vol. 1, No. 3, Jul. 1, 2001, pp. 357-378(22).

Casares, S. et al., Modulation of CD4 T cell function by soluble MHC II-peptide chimeras, Journal International Reviews of Immunology, vol. 20, 2001—Issue 5, pp. 547-573.

Davis MM, Bjorkman PJ. T-cell antigen receptor genes and T-cell recognition. Nature. 1988;334(6181):395-402. Epub Aug. 4, 1988. doi: 10.1038/334395a0. PubMed PMID: 3043226.

Fantini MC, Dominitzki S, Rizzo A, Neurath MF, Becker C. In vitro generation of CD4+ CD25+ regulatory cells from murine naive T cells. Nature protocols. 2007;2(7):1789-94. doi: 10.1038/nprot.2007.258. PubMed PMID: 17641646.

G Dotti, HE Heslop, Current status of genetic modification of T cells for cancer treatment—Cytotherapy, 2005; 7(3):262-72.

Hammad H, Lambrecht BN. Dendritic cells and epithelial cells: linking innate and adaptive immunity in asthma. Nat Rev Immunol. 2008;8(3):193-204. doi: 10.1038/nri2275. PubMed PMID: 18301423.

Hammad H, Plantinga M, Deswarte K, Pouliot P, Willart MA, Kool M, Muskens F, Lambrecht BN. Inflammatory dendritic cells—not basophils—are necessary and sufficient for induction of Th2 immunity to inhaled house dust mite allergen. J Exp Med. 2010;207(10):2097-111. doi: 10.1084/jem.20101563. PubMed PMID: 20819925; PMCID: 2947072.

Harris SJ, Roth JF, Savage N, Woodrow SA, Hemingway IK, Hoyne GF, Lamb JR, Layton GT. Prediction of murine MHC class I epitopes in a major house dust mite allergen and induction of T1-type CD8+ T cell responses. Int Immunol. 1997;9(2):273-80. PubMed PMID: 9040009.

Kuhns MS, Badgandi HB. Piecing together the family portrait of TCR-CD3 complexes. Immunological Reviews. 2012;250.

Kuhns MS, Davis MM, Garcia KC. Deconstructing the Form and Function of the TCR/CD3 Complex. Immunity. 2006;24(2)133-9. PubMed PMID: 16473826.

Kuhns MS, Davis MM. TCR signaling emerges from the sum of many parts. Frontiers in Immunology. 2012;3. doi: 10.3389/fimmu.2012.00159.

Lambrecht BN, Hammad H. The immunology of asthma. Nature Immunology. 2015;16(1):45-56.

Mathis D, Benoist C. Levees of immunological tolerance. Nature immunology. 2010;11(1):3-6. Epub Dec. 18, 2009. doi: 10.1038/ni.1833. PubMed PMID: 20016503.

Maus MV, Grupp SA, Porter DL, June CH. Antibody-modified T cells: CARs take the front seat for hematologic malignancies. Blood. 2014;123(17):2625-35. doi: 10.1182/blood-2013-11-492231. PubMed PMID: 24578504; PMCID: 3999751.

Meyers JH, Chakravarti S, Schlesinger D, Illes Z, Waldner H, Umetsu SE, Kenny J, Zheng XX, Umetsu DT, Dekruyff RH, Strom TB, Kuchroo VK. TIM-4 is the ligand for TIM-1, and the TIM-1-TIM-4 interaction regulates T cell proliferation. Nat Immunol. 2005;6(5):455-64. doi: 10.1038/ni1185. PubMed PMID: 15793576.

Moon JJ, Chu HH, Pepper M, McSorley SJ, Jameson SC, Kedl RM, Jenkins MK. Naive CD4(+) T cell frequency varies for different epitopes and predicts repertoire diversity and response magnitude. Immunity. 2007;27 (2):203-13. Epub Aug. 21, 2007. doi: S1074-7613(07)00366-4 [pii] 10.1016/j.immuni.2007.07.007. PubMed PMID: 17707129.

Savoldo B, Dotti G. Chimeric antigen receptors (CARs) from bench-to-bedside. Immunol Lett. 2013;155(1-2):40-2. doi: 10.1016/j.imlet.2013.09.014. PubMed PMID: 24080488; PMCID: 3926092.

Uttenthal BJ, Chua I, Morris EC, Stauss HJ. Challenges in T cell receptor gene therapy. The journal of gene medicine. 2012;14(6):386-99. doi: 10.1002/jgm.2637. PubMed PMID: 22610778.

Vercelli D. Discovering susceptibility genes for asthma and allergy. Nature reviews Immunology. 2008;8(3):169-82. Epub Feb. 28, 2008. doi: 10.1038/nri2257. PubMed PMID: 18301422.

Willart MA, Deswarte K, Pouliot P, Braun H, Beyaert R, Lambrecht BN, Hammad H. Interleukin-1alpha controls allergic sensitization to inhaled house dust mite via the epithelial release of GM-CSF and IL-33. J Exp Med. 2012;209(8)1505-17. doi: 10.1084/jem.20112691. PubMed PMID: 22802353; PMCID: 3409497.

Willemsen, RA et al. A phage display selected Fab fragment with MHC class I-restricted specificity for MAGE-A1 allows for retargeting of primary human T lymphocytes, Gene Therapy 8, 1601-1608 (2001).

Wu HJ, Ivanov, II, Darce J, Hattori K, Shima T, Umesaki Y, Littman DR, Benoist C, Mathis D. Gut-residing segmented filamentous bacteria drive autoimmune arthritis via T helper 17 cells. Immunity. 2010;32(6):815-27. Epub Jul. 14, 2010. doi: 10.1016/j.immuni.2010.06.001. PubMed PMID: 20620945; PMCID: 2904693.

Jackson et al. Targeting CD8+ T-Cell Tolerance for Cancer Immunotherapy. Immunotherapy. Jul. 2014; 6(7): 833-852. doi:10.2217/imt.14.51.

Sharpe et al. Genetically modified T cells in cancer therapy: opportunities and challenges. Dis Model Mech. Apr. 2015; 8(4): 337-350.

Zanetti. Tapping CD4 T Cells for Cancer Immunotherapy: The Choice of Personalized Genomics. J Immunol Mar. 1, 2015, 194 (5) 2049-2056.

Qian, Z et al. Engineered Tregulatory Cells Co-expressing MHC Class II:peptide Complexes Are Efficient Inhibitors of Autoimmune T Cell Function and Prevent the Development of Autoimmune Arthritis. J. Immunol. Author manuscript. Jun. 1, 2014, vol. 190; pp. 1-23; abstract; p. 3, fifth paragraph-p. 4, first paragraph; p. 6, fourth paragraph; doi:1 OA049/jimmunol. 1300024.

Thiel, M et al. Efficiency of T-cell Costimulation by CD80 and CD86 Cross-linking Correlates With Calcium Entry. Immunology. 2009, vol. 129, pp. 28-40; p. 26, first column, first paragraph-second column, first paragraph; p. 28, second column, second paragraph; p. 29, first column, third paragraph; p. 32, first column, first paragraph; doi:1 0.1111/j.1365-2567 .2009.03155.x.

Bueno, C et al. T Cell Signalling Induced by Bacterial Superantigens. Chemical Immunology and Allergy. Feb. 2007. vol. 93. pp. 161-180. 001: 10.1159/0000100894; p. 171, third paragraph; p. 172. first paragraph.

(56) References Cited

OTHER PUBLICATIONS

Podojil, JR et al. Molecular Mechanisms of T Cell Receptor and Costimulatory Molecule Ligation/Blockade in Autoimmune Disease Therapy. Immunol Rev. Author manuscript. May 1, 2010. vol. 229. pp. 1-28. doi:10.1111/i.1600-065X.2009.00773.x; p. 2. first paragraph; p. 11. second paragraph.

\* cited by examiner (i)

(ii)

(iii)

(iv)

CD80/CD86-Lck Chimera

SEQUENCE LISTING

<160> NUMBER OF SEQ ID NOS: 39

<210> SEQ ID NO 1
<211> LENGTH: 365

```
<212> TYPE: PRT
<213> ORGANISM: Homo sapiens

<400> SEQUENCE: 1

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Tyr Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Arg Asn Thr Arg Asn Val Lys Ala Gln Ser Gln
                85                  90                  95

Thr Asp Arg Val Asp Leu Gly Thr Leu Arg Gly Tyr Tyr Asn Gln Ser
            100                 105                 110

Glu Ala Gly Ser His Thr Ile Gln Met Met Tyr Gly Cys Asp Val Gly
        115                 120                 125

Ser Asp Gly Arg Phe Leu Arg Gly Tyr Arg Gln Asp Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Trp Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Val Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 2
<211> LENGTH: 362
<212> TYPE: PRT
<213> ORGANISM: Homo sapiens
```

<400> SEQUENCE: 2

```
Met Arg Val Thr Ala Pro Arg Thr Val Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
50                  55                  60

Ala Ser Pro Arg Thr Glu Pro Arg Ala Pro Trp Ile Glu Gln Glu Gly
65                  70                  75                  80

Pro Glu Tyr Trp Asp Arg Asn Thr Gln Ile Phe Lys Thr Asn Thr Gln
                85                  90                  95

Thr Tyr Arg Glu Asn Leu Arg Ile Ala Leu Arg Tyr Tyr Asn Gln Ser
            100                 105                 110

Glu Ala Gly Ser His Thr Trp Gln Thr Met Tyr Gly Cys Asp Val Gly
            115                 120                 125

Pro Asp Gly Arg Leu Leu Arg Gly His Asn Gln Tyr Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Leu Cys Val Glu Trp Leu
            180                 185                 190

Arg Arg His Leu Glu Asn Gly Lys Glu Thr Leu Gln Arg Ala Asp Pro
            195                 200                 205

Pro Lys Thr His Val Thr His His Pro Val Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
290                 295                 300

Thr Ile Pro Ile Val Gly Ile Val Ala Gly Leu Ala Val Leu Ala Val
305                 310                 315                 320

Val Val Ile Gly Ala Val Val Ala Thr Val Met Cys Arg Arg Lys Ser
                325                 330                 335

Ser Gly Gly Lys Gly Gly Ser Tyr Ser Gln Ala Ala Ser Ser Asp Ser
            340                 345                 350

Ala Gln Gly Ser Asp Val Ser Leu Thr Ala
            355                 360
```

<210> SEQ ID NO 3
<211> LENGTH: 366
<212> TYPE: PRT
<213> ORGANISM: Homo sapiens

<400> SEQUENCE: 3

Met Arg Val Met Ala Pro Arg Thr Leu Ile Leu Leu Leu Ser Gly Ala
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Ala Asp Arg Val Asn Leu Arg Lys Leu Arg Gly Tyr Tyr Asn Gln Ser
            100                 105                 110

Glu Asp Gly Ser His Thr Leu Gln Trp Met Tyr Gly Cys Asp Leu Gly
        115                 120                 125

Pro Asp Gly Arg Leu Leu Arg Gly Tyr Asp Gln Ser Ala Tyr Asp Gly
130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Glu Pro Ser Ser Gln Pro
290                 295                 300

Thr Ile Pro Ile Val Gly Ile Val Ala Gly Leu Ala Val Leu Ala Val
305                 310                 315                 320

Leu Ala Val Leu Gly Ala Val Met Ala Val Met Cys Arg Arg Lys
                325                 330                 335

Ser Ser Gly Gly Lys Gly Gly Ser Cys Ser Gln Ala Ala Ser Ser Asn
            340                 345                 350

Ser Ala Gln Gly Ser Asp Glu Ser Leu Ile Ala Cys Lys Ala
        355                 360                 365

<210> SEQ ID NO 4
<211> LENGTH: 260
<212> TYPE: PRT
<213> ORGANISM: Homo sapiens

<400> SEQUENCE: 4

Met Arg Pro Glu Asp Arg Met Phe His Ile Arg Ala Val Ile Leu Arg

-continued

```
                1               5                    10                   15
            Ala Leu Ser Leu Ala Phe Leu Leu Ser Leu Arg Gly Ala Gly Ala Ile
                            20                  25                  30

Lys Ala Asp His Val Ser Thr Tyr Ala Ala Phe Val Gln Thr His Arg
                            35                  40                  45

Pro Thr Gly Glu Phe Met Phe Glu Asp Glu Met Phe Tyr
                            50                  55                  60

Val Asp Leu Asp Lys Lys Glu Thr Val Trp His Leu Glu Glu Phe Gly
            65                  70                  75                  80

Gln Ala Phe Ser Phe Glu Ala Gln Gly Gly Leu Ala Asn Ile Ala Ile
                            85                  90                  95

Leu Asn Asn Asn Leu Asn Thr Leu Ile Gln Arg Ser Asn His Thr Gln
                            100                 105                 110

Ala Thr Asn Asp Pro Pro Glu Val Thr Val Phe Pro Lys Glu Pro Val
                            115                 120                 125

Glu Leu Gly Gln Pro Asn Thr Leu Ile Cys His Ile Asp Lys Phe Phe
                            130                 135                 140

Pro Pro Val Leu Asn Val Thr Trp Leu Cys Asn Gly Glu Leu Val Thr
            145                 150                 155                 160

Glu Gly Val Ala Glu Ser Leu Phe Leu Pro Arg Thr Asp Tyr Ser Phe
                            165                 170                 175

His Lys Phe His Tyr Leu Thr Phe Val Pro Ser Ala Gly Asp Phe Tyr
                            180                 185                 190

Asp Cys Arg Val Glu His Trp Gly Leu Asp Gln Pro Leu Leu Lys His
                            195                 200                 205

Trp Glu Ala Gln Glu Pro Ile Gln Met Pro Glu Thr Thr Glu Thr Val
                            210                 215                 220

Leu Cys Ala Leu Gly Leu Val Leu Gly Leu Val Gly Ile Ile Val Gly
            225                 230                 235                 240

Thr Val Leu Ile Ile Lys Ser Leu Arg Ser Gly His Asp Pro Arg Ala
                            245                 250                 255

Gln Gly Thr Leu
                            260

<210> SEQ ID NO 5
<211> LENGTH: 258
<212> TYPE: PRT
<213> ORGANISM: Homo sapiens

<400> SEQUENCE: 5

Met Met Val Leu Gln Val Ser Ala Ala Pro Arg Thr Val Ala Leu Thr
            1               5                   10                  15

Ala Leu Leu Met Val Leu Leu Thr Ser Val Val Gln Gly Arg Ala Thr
                            20                  25                  30

Pro Glu Asn Tyr Leu Phe Gln Gly Arg Gln Glu Cys Tyr Ala Phe Asn
                            35                  40                  45

Gly Thr Gln Arg Phe Leu Glu Arg Tyr Ile Tyr Asn Arg Glu Glu Phe
                            50                  55                  60

Ala Arg Phe Asp Ser Asp Val Gly Glu Phe Arg Ala Val Thr Glu Leu
            65                  70                  75                  80

Gly Arg Pro Ala Ala Glu Tyr Trp Asn Ser Gln Lys Asp Ile Leu Glu
                            85                  90                  95

Glu Lys Arg Ala Val Pro Asp Arg Met Cys Arg His Asn Tyr Glu Leu
                            100                 105                 110
```

```
Gly Gly Pro Met Thr Leu Gln Arg Arg Val Gln Pro Arg Val Asn Val
            115                 120                 125

Ser Pro Ser Lys Lys Gly Pro Leu Gln His His Asn Leu Leu Val Cys
130                 135                 140

His Val Thr Asp Phe Tyr Pro Gly Ser Ile Gln Val Arg Trp Phe Leu
145                 150                 155                 160

Asn Gly Gln Glu Glu Thr Ala Gly Val Val Ser Thr Asn Leu Ile Arg
                165                 170                 175

Asn Gly Asp Trp Thr Phe Gln Ile Leu Val Met Leu Glu Met Thr Pro
                180                 185                 190

Gln Gln Gly Asp Val Tyr Thr Cys Gln Val Glu His Thr Ser Leu Asp
            195                 200                 205

Ser Pro Val Thr Val Glu Trp Lys Ala Gln Ser Asp Ser Ala Arg Ser
210                 215                 220

Lys Thr Leu Thr Gly Ala Gly Gly Phe Val Leu Gly Leu Ile Ile Cys
225                 230                 235                 240

Gly Val Gly Ile Phe Met His Arg Arg Ser Lys Lys Val Gln Arg Gly
                245                 250                 255

Ser Ala

<210> SEQ ID NO 6
<211> LENGTH: 254
<212> TYPE: PRT
<213> ORGANISM: Homo sapiens

<400> SEQUENCE: 6

Met Ile Leu Asn Lys Ala Leu Met Leu Gly Ala Leu Ala Leu Thr Thr
1               5                   10                  15

Val Met Ser Pro Cys Gly Gly Glu Asp Ile Val Ala Asp His Val Ala
                20                  25                  30

Ser Tyr Gly Val Asn Leu Tyr Gln Ser Tyr Gly Pro Ser Gly Gln Tyr
            35                  40                  45

Thr His Glu Phe Asp Gly Asp Glu Gln Phe Tyr Val Asp Leu Gly Arg
        50                  55                  60

Lys Glu Thr Val Trp Cys Leu Pro Val Leu Arg Gln Phe Arg Phe Asp
65                  70                  75                  80

Pro Gln Phe Ala Leu Thr Asn Ile Ala Val Leu Lys His Asn Leu Asn
                85                  90                  95

Ser Leu Ile Lys Arg Ser Asn Ser Thr Ala Ala Thr Asn Glu Val Pro
            100                 105                 110

Glu Val Thr Val Phe Ser Lys Ser Pro Val Thr Leu Gly Gln Pro Asn
        115                 120                 125

Ile Leu Ile Cys Leu Val Asp Asn Ile Phe Pro Pro Val Val Asn Ile
    130                 135                 140

Thr Trp Leu Ser Asn Gly His Ser Val Thr Glu Gly Val Ser Glu Thr
145                 150                 155                 160

Ser Phe Leu Ser Lys Ser Asp His Ser Phe Phe Lys Ile Ser Tyr Leu
                165                 170                 175

Thr Leu Leu Pro Ser Ala Glu Glu Ser Tyr Asp Cys Lys Val Glu His
            180                 185                 190

Trp Gly Leu Asp Lys Pro Leu Leu Lys His Trp Glu Pro Glu Ile Pro
        195                 200                 205

Ala Pro Met Ser Glu Leu Thr Glu Thr Val Val Cys Ala Leu Gly Leu
    210                 215                 220
```

Ser Val Gly Leu Val Gly Ile Val Val Gly Thr Val Phe Ile Ile Arg
225                 230                 235                 240

Gly Leu Arg Ser Val Gly Ala Ser Arg His Gln Gly Pro Leu
            245                 250

<210> SEQ ID NO 7
<211> LENGTH: 261
<212> TYPE: PRT
<213> ORGANISM: Homo sapiens

<400> SEQUENCE: 7

Met Ser Trp Lys Lys Ala Leu Arg Ile Pro Gly Gly Leu Arg Ala Ala
1               5                   10                  15

Thr Val Thr Leu Met Leu Ala Met Leu Ser Thr Pro Val Ala Glu Gly
            20                  25                  30

Arg Asp Ser Pro Glu Asp Phe Val Tyr Gln Phe Lys Ala Met Cys Tyr
        35                  40                  45

Phe Thr Asn Gly Thr Glu Arg Val Arg Tyr Val Thr Arg Tyr Ile Tyr
    50                  55                  60

Asn Arg Glu Glu Tyr Ala Arg Phe Asp Ser Asp Val Glu Val Tyr Arg
65                  70                  75                  80

Ala Val Thr Pro Leu Gly Pro Pro Asp Ala Glu Tyr Trp Asn Ser Gln
                85                  90                  95

Lys Glu Val Leu Glu Arg Thr Arg Ala Glu Leu Asp Thr Val Cys Arg
            100                 105                 110

His Asn Tyr Gln Leu Glu Leu Arg Thr Thr Leu Gln Arg Arg Val Glu
        115                 120                 125

Pro Thr Val Thr Ile Ser Pro Ser Arg Thr Glu Ala Leu Asn His His
    130                 135                 140

Asn Leu Leu Val Cys Ser Val Thr Asp Phe Tyr Pro Ala Gln Ile Lys
145                 150                 155                 160

Val Arg Trp Phe Arg Asn Asp Gln Glu Glu Thr Thr Gly Val Val Ser
                165                 170                 175

Thr Pro Leu Ile Arg Asn Gly Asp Trp Thr Phe Gln Ile Leu Val Met
            180                 185                 190

Leu Glu Met Thr Pro Gln His Gly Asp Val Tyr Thr Cys His Val Glu
        195                 200                 205

His Pro Ser Leu Gln Asn Pro Ile Thr Val Glu Trp Arg Ala Gln Ser
    210                 215                 220

Glu Ser Ala Gln Ser Lys Met Leu Ser Gly Ile Gly Gly Phe Val Leu
225                 230                 235                 240

Gly Leu Ile Phe Leu Gly Leu Gly Leu Ile Ile His His Arg Ser Gln
                245                 250                 255

Lys Gly Leu Leu His
            260

<210> SEQ ID NO 8
<211> LENGTH: 254
<212> TYPE: PRT
<213> ORGANISM: Homo sapiens

<400> SEQUENCE: 8

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

-continued

Ile Gln Ala Glu Phe Tyr Leu Asn Pro Asp Gln Ser Gly Glu Phe Met
             35                  40                  45

Phe Asp Phe Asp Gly Asp Glu Ile Phe His Val Asp Met Ala Lys Lys
 50                  55                  60

Glu Thr Val Trp Arg Leu Glu Glu Phe Gly Arg Phe Ala Ser Phe Glu
 65                  70                  75                  80

Ala Gln Gly Ala Leu Ala Asn Ile Ala Val Asp Lys Ala Asn Leu Glu
                 85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
            115                 120                 125

Val Leu Ile Cys Phe Ile Asp Lys Phe Thr Pro Pro Val Val Asn Val
130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
            195                 200                 205

Ser Pro Leu Pro Glu Thr Thr Glu Asn Val Val Cys Ala Leu Gly Leu
            210                 215                 220

Thr Val Gly Leu Val Gly Ile Ile Ile Gly Thr Ile Phe Ile Ile Lys
225                 230                 235                 240

Gly Val Arg Lys Ser Asn Ala Ala Glu Arg Arg Gly Pro Leu
                245                 250

<210> SEQ ID NO 9
<211> LENGTH: 266
<212> TYPE: PRT
<213> ORGANISM: Homo sapiens

<400> SEQUENCE: 9

Met Val Cys Leu Arg Leu Pro Gly Gly Ser Cys Met Ala Val Leu Thr
 1               5                  10                  15

Val Thr Leu Met Val Leu Ser Ser Pro Leu Ala Leu Ala Gly Asp Thr
                 20                  25                  30

Arg Pro Arg Phe Leu Glu Glu Val Lys Phe Glu Cys His Phe Phe Asn
             35                  40                  45

Gly Thr Glu Arg Val Arg Leu Leu Glu Arg Arg Val His Asn Gln Glu
 50                  55                  60

Glu Tyr Ala Arg Tyr Asp Ser Asp Val Gly Glu Tyr Arg Ala Val Thr
 65                  70                  75                  80

Glu Leu Gly Arg Pro Asp Ala Glu Tyr Trp Asn Ser Gln Lys Asp Leu
                 85                  90                  95

Leu Glu Arg Arg Arg Ala Ala Val Asp Thr Tyr Cys Arg His Asn Tyr
            100                 105                 110

Gly Val Gly Glu Ser Phe Thr Val Gln Arg Arg Val Gln Pro Lys Val
            115                 120                 125

Thr Val Tyr Pro Ser Lys Thr Gln Pro Leu Gln His His Asn Leu Leu
130                 135                 140

Val Cys Ser Val Asn Gly Phe Tyr Pro Gly Ser Ile Glu Val Arg Trp
145                 150                 155                 160

```
Phe Arg Asn Gly Gln Glu Lys Thr Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Gln Ser Gly Glu Val Tyr Thr Cys Gln Val Glu His Pro Ser
        195                 200                 205

Val Met Ser Pro Leu Thr Val Glu Trp Arg Ala Arg Ser Glu Ser Ala
210                 215                 220

Gln Ser Lys Met Leu Ser Gly Val Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Pro Pro Thr Gly Phe Leu Ser
            260                 265
```

<210> SEQ ID NO 10
<211> LENGTH: 250
<212> TYPE: PRT
<213> ORGANISM: Mus musculus

<400> SEQUENCE: 10

```
Arg Ser Arg Ala Leu Ile Leu Gly Val Leu Ala Leu Thr Thr Met Leu
1               5                   10                  15

Ser Leu Cys Gly Gly Glu Asp Tyr Ile Glu Ala Asp His Val Ala Phe
                20                  25                  30

Tyr Gly Ile Ser Val Tyr Gln Ser Pro Gly Asp Ile Gly Gln Tyr Thr
            35                  40                  45

Phe Glu Phe Asp Gly Asp Glu Leu Phe Tyr Val Asp Leu Asp Lys Lys
        50                  55                  60

Glu Thr Val Trp Met Leu Pro Glu Phe Gly Gln Leu Thr Ser Phe Asp
65                  70                  75                  80

Pro Gln Gly Gly Leu Gln Glu Ile Ala Thr Gly Lys Tyr Asn Leu Glu
                85                  90                  95

Ile Leu Ile Lys Asp Ser Asn Phe Thr Pro Ala Ala Asn Glu Ala Pro
            100                 105                 110

Gln Ala Thr Val Phe Pro Lys Ser Pro Val Leu Leu Gly Gln Pro Asn
        115                 120                 125

Thr Leu Ile Cys Phe Val Asp Asn Ile Phe Pro Pro Val Ile Asn Ile
130                 135                 140

Thr Trp Leu Arg Asn Ser Lys Ser Val Thr Asp Gly Val Tyr Glu Thr
145                 150                 155                 160

Ser Phe Leu Val Asn Arg Asp His Ser Phe His Lys Leu Ser Tyr Leu
                165                 170                 175

Thr Phe Ile Pro Ser Asp Asp Ile Tyr Asp Cys Lys Val Glu His
            180                 185                 190

Trp Gly Leu Glu Glu Pro Val Leu Lys His Trp Glu Pro Glu Ile Pro
        195                 200                 205

Ala Pro Met Ser Glu Leu Thr Glu Thr Val Ile Cys Ala Leu Gly Leu
210                 215                 220

Ser Val Gly Leu Val Gly Ile Val Val Gly Thr Ile Phe Ile Ile Gln
225                 230                 235                 240

Gly Leu Arg Ser Gly Gly Thr Ser Arg His
                245                 250
```

-continued

<210> SEQ ID NO 11
<211> LENGTH: 349
<212> TYPE: PRT
<213> ORGANISM: Mus musculus

<400> SEQUENCE: 11

Met Ala Gln Arg Thr Leu Phe Leu Leu Ala Ala Leu Thr Met
1               5                   10                  15

Ile Glu Thr Arg Ala Gly Pro His Ser Met Arg Tyr Phe Glu Thr Ala
            20                  25                  30

Val Phe Arg Pro Gly Leu Gly Glu Pro Arg Phe Ile Ser Val Gly Tyr
        35                  40                  45

Val Asp Asn Thr Gln Phe Val Ser Phe Asp Ser Asp Ala Glu Asn Pro
    50                  55                  60

Arg Ser Glu Pro Arg Ala Pro Trp Met Glu Gln Glu Gly Pro Glu Tyr
65                  70                  75                  80

Trp Glu Arg Glu Thr Gln Ile Ala Lys Asp Asn Glu Gln Ser Phe Gly
                85                  90                  95

Trp Ser Leu Arg Asn Leu Ile His Tyr Tyr Asn Gln Ser Lys Gly Gly
            100                 105                 110

Phe His Thr Phe Gln Arg Leu Ser Gly Cys Asp Met Gly Leu Asp Gly
        115                 120                 125

Arg Leu Leu Arg Gly Tyr Leu Gln Phe Ala Tyr Asp Gly Arg Asp Tyr
130                 135                 140

Ile Thr Leu Asn Glu Asp Leu Lys Thr Trp Met Ala Ala Asp Leu Val
145                 150                 155                 160

Ala Leu Ile Thr Arg Arg Lys Trp Glu Gln Ala Gly Ala Ala Glu Leu
                165                 170                 175

Tyr Lys Phe Tyr Leu Glu Gly Glu Cys Val Glu Trp Leu Arg Arg Tyr
            180                 185                 190

Leu Glu Leu Gly Asn Glu Thr Leu Leu Arg Thr Asp Pro Pro Lys Ala
        195                 200                 205

His Val Thr His His Pro Arg Pro Ala Gly Asp Val Thr Leu Arg Cys
    210                 215                 220

Trp Ala Leu Gly Phe Tyr Pro Ala Asp Ile Thr Leu Thr Trp Gln Leu
225                 230                 235                 240

Asn Gly Glu Glu Leu Thr Gln Asp Met Glu Leu Val Glu Thr Arg Pro
                245                 250                 255

Ala Gly Asp Gly Thr Phe Gln Lys Trp Ala Ala Val Val Pro Leu
            260                 265                 270

Gly Lys Glu Gln Asn Tyr Thr Cys His Val Tyr His Glu Gly Leu Pro
        275                 280                 285

Glu Pro Leu Thr Leu Arg Trp Glu Pro Pro Ser Thr Gly Ser Asn
    290                 295                 300

Met Val Asn Ile Ala Val Leu Val Leu Gly Ala Val Ile Ile Ile
305                 310                 315                 320

Glu Ala Met Val Ala Phe Val Leu Lys Ser Ser Arg Lys Ile Ala Ile
                325                 330                 335

Leu Pro Gly Pro Ala Gly Thr Lys Gly Ser Ser Ala Ser
            340                 345

<210> SEQ ID NO 12
<211> LENGTH: 350
<212> TYPE: PRT
<213> ORGANISM: Mus musculus

<400> SEQUENCE: 12

Met Ala Pro Cys Thr Leu Leu Leu Leu Ala Ala Leu Ala Pro
1               5                   10                  15

Thr Gln Thr Arg Ala Ala Arg Ala Ala Ala Arg Gly Pro Val Arg Arg
            20                  25                  30

Ser Gly Ser His Arg Ala Pro Pro Gly Pro His Ser Leu Ser Asp
            35                  40                  45

Ala Asp Asn Pro Arg Phe Glu Pro Arg Ala Pro Trp Met Glu Gln Glu
50                  55                  60

Gly Pro Glu Tyr Trp Glu Gln Thr Gln Arg Ala Lys Ser Asp Glu
65                  70                  75                  80

Gln Trp Phe Arg Val Ser Leu Arg Thr Ala Gln Arg Tyr Tyr Asn Gln
                85                  90                  95

Ser Lys Gly Gly Ser His Thr Phe Gln Arg Met Phe Gly Cys Asp Val
            100                 105                 110

Gly Ser Asp Trp Arg Leu Leu Arg Gly Tyr Gln Gln Phe Ala Tyr Asp
            115                 120                 125

Gly Arg Asp Tyr Ile Ala Leu Asn Glu Asp Leu Lys Thr Trp Thr Ala
130                 135                 140

Ala Asp Thr Ala Ala Leu Ile Thr Arg Arg Lys Trp Glu Gln Ala Gly
145                 150                 155                 160

Asp Ala Glu Tyr Tyr Arg Ala Tyr Leu Glu Gly Glu Cys Val Glu Trp
                165                 170                 175

Leu Arg Arg Tyr Leu Glu Leu Gly Asn Glu Thr Leu Leu Arg Thr Asp
            180                 185                 190

Ser Pro Lys Ala His Val Thr Tyr His Pro Arg Ser Gln Val Asp Val
            195                 200                 205

Thr Leu Arg Cys Trp Ala Leu Gly Phe Tyr Pro Ala Asp Ile Thr Leu
210                 215                 220

Thr Trp Gln Leu Asn Gly Glu Asp Leu Thr Gln Asp Met Glu Leu Val
225                 230                 235                 240

Glu Thr Arg Pro Ala Gly Asp Gly Thr Phe Gln Lys Trp Ala Ala Val
                245                 250                 255

Val Val Pro Leu Gly Lys Glu Gln Asn Tyr Thr Cys His Val His His
            260                 265                 270

Lys Gly Leu Pro Glu Pro Leu Thr Leu Arg Trp Lys Leu Pro Pro Pro
            275                 280                 285

Thr Val Ser Asn Thr Val Ile Ile Ala Val Leu Val Val Leu Gly Ala
            290                 295                 300

Ala Ile Val Thr Gly Ala Val Val Ala Phe Val Met Lys Met Arg Arg
305                 310                 315                 320

Asn Thr Gly Gly Lys Gly Val Asn Tyr Ala Leu Ala Pro Gly Ser Gln
                325                 330                 335

Thr Ser Asp Leu Ser Leu Pro Asp Gly Lys Val Met Val His
            340                 345                 350

<210> SEQ ID NO 13
<211> LENGTH: 264
<212> TYPE: PRT
<213> ORGANISM: Mus musculus

<400> SEQUENCE: 13

Met Val Trp Leu Pro Arg Val Pro Cys Val Ala Ala Val Ile Leu Leu
1               5                   10                  15

```
Leu Thr Val Leu Ser Pro Pro Met Ala Leu Val Arg Asp Ser Arg Pro
             20                  25                  30

Trp Phe Leu Glu Tyr Cys Lys Ser Glu Cys His Phe Tyr Asn Gly Thr
             35                  40                  45

Gln Arg Val Arg Leu Leu Glu Arg Tyr Phe Tyr Asn Leu Glu Glu Asn
         50                  55                  60

Leu Arg Phe Asp Ser Asp Val Gly Glu Phe His Ala Val Thr Glu Leu
 65                  70                  75                  80

Gly Arg Pro Asp Ala Glu Asn Trp Asn Ser Gln Pro Glu Phe Leu Glu
                 85                  90                  95

Gln Lys Arg Ala Glu Val Asp Thr Val Cys Arg His Asn Tyr Glu Ile
             100                 105                 110

Ser Asp Lys Phe Leu Val Arg Arg Val Glu Pro Thr Val Thr Val
         115                 120                 125

Tyr Pro Thr Lys Thr Gln Pro Leu Glu His His Asn Leu Leu Val Cys
130                 135                 140

Ser Val Ser Asp Phe Tyr Pro Gly Asn Ile Glu Val Arg Trp Phe Arg
145                 150                 155                 160

Asn Gly Lys Glu Glu Lys Thr Gly Ile Val Ser Thr Gly Leu Val Arg
                 165                 170                 175

Asn Gly Asp Trp Thr Phe Gln Thr Leu Val Met Leu Glu Thr Val Pro
             180                 185                 190

Gln Ser Gly Glu Val Tyr Thr Cys Gln Val Glu His Pro Ser Leu Thr
         195                 200                 205

Asp Pro Val Thr Val Glu Trp Lys Ala Gln Ser Thr Ser Ala Gln Asn
210                 215                 220

Lys Met Leu Ser Gly Val Gly Phe Val Leu Gly Leu Leu Phe Leu
225                 230                 235                 240

Gly Ala Gly Leu Phe Ile Tyr Phe Arg Asn Gln Lys Gly Gln Ser Gly
                 245                 250                 255

Leu Gln Pro Thr Gly Leu Leu Ser
             260

<210> SEQ ID NO 14
<211> LENGTH: 255
<212> TYPE: PRT
<213> ORGANISM: Mus musculus

<400> SEQUENCE: 14

Met Ala Thr Ile Gly Ala Leu Val Leu Arg Phe Phe Ile Ala Val
 1               5                  10                  15

Leu Met Ser Ser Gln Lys Ser Trp Ala Ile Lys Glu Glu His Thr Ile
             20                  25                  30

Ile Gln Ala Glu Phe Tyr Leu Leu Pro Asp Lys Arg Gly Glu Phe Met
             35                  40                  45

Phe Asp Phe Asp Gly Asp Glu Ile Phe His Val Asp Ile Glu Lys Ser
         50                  55                  60

Glu Thr Ile Trp Arg Leu Glu Glu Phe Ala Lys Phe Ala Ser Phe Glu
 65                  70                  75                  80

Ala Gln Gly Ala Leu Ala Asn Ile Ala Val Asp Lys Ala Asn Leu Asp
                 85                  90                  95

Val Met Lys Glu Arg Ser Asn Asn Thr Pro Asp Ala Asn Val Ala Pro
             100                 105                 110

Glu Val Thr Val Leu Ser Arg Ser Pro Val Asn Leu Gly Glu Pro Asn
             115                 120                 125
```

-continued

```
Ile Leu Ile Cys Phe Ile Asp Lys Phe Ser Pro Val Val Asn Val
            130                 135                 140

Thr Trp Leu Arg Asn Gly Arg Pro Val Thr Glu Gly Val Ser Glu Thr
145                 150                 155                 160

Val Phe Leu Pro Arg Asp Asp His Leu Phe Arg Lys Phe His Tyr Leu
                165                 170                 175

Thr Phe Leu Pro Ser Thr Asp Asp Phe Tyr Asp Cys Glu Val Asp His
            180                 185                 190

Trp Gly Leu Glu Glu Pro Leu Arg Lys His Trp Glu Phe Glu Glu Lys
        195                 200                 205

Thr Leu Leu Pro Glu Thr Lys Glu Asn Val Val Cys Ala Leu Gly Leu
210                 215                 220

Phe Val Gly Leu Val Gly Ile Val Val Gly Ile Ile Leu Ile Met Lys
225                 230                 235                 240

Gly Ile Lys Lys Arg Asn Val Val Glu Arg Arg Gln Gly Ala Leu
                245                 250                 255

<210> SEQ ID NO 15
<211> LENGTH: 263
<212> TYPE: PRT
<213> ORGANISM: Mus musculus

<400> SEQUENCE: 15

Met Trp Leu Pro Arg Val Pro Cys Val Ala Ala Val Ile Leu Leu Leu
1               5                   10                  15

Thr Val Leu Ser Pro Pro Val Ala Leu Val Arg Asp Ser Arg Pro Trp
            20                  25                  30

Phe Leu Glu Tyr Cys Lys Ser Glu Cys His Phe Tyr Asn Gly Thr Gln
        35                  40                  45

Arg Val Arg Leu Leu Val Arg Tyr Phe Tyr Asn Leu Glu Glu Asn Leu
50                  55                  60

Arg Phe Asp Ser Asp Val Gly Glu Phe Arg Ala Val Thr Glu Leu Gly
65                  70                  75                  80

Arg Pro Asp Ala Glu Asn Trp Asn Ser Gln Pro Glu Phe Leu Glu Gln
                85                  90                  95

Lys Arg Ala Glu Val Asp Thr Val Cys Arg His Asn Tyr Glu Ile Phe
            100                 105                 110

Asp Asn Phe Leu Val Pro Arg Arg Val Glu Pro Thr Val Thr Val Tyr
        115                 120                 125

Pro Thr Lys Thr Gln Pro Leu Glu His His Asn Leu Leu Val Cys Ser
130                 135                 140

Val Ser Asp Phe Tyr Pro Gly Asn Ile Glu Val Arg Trp Phe Arg Asn
145                 150                 155                 160

Gly Lys Glu Glu Lys Thr Gly Ile Val Ser Thr Gly Leu Val Arg Asn
                165                 170                 175

Gly Asp Trp Thr Phe Gln Thr Leu Val Met Leu Glu Thr Val Pro Gln
            180                 185                 190

Ser Gly Glu Val Tyr Thr Cys Gln Val Glu His Pro Ser Leu Thr Asp
        195                 200                 205

Pro Val Thr Val Glu Trp Lys Ala Gln Ser Thr Ser Ala Gln Asn Lys
210                 215                 220

Met Leu Ser Gly Val Gly Gly Phe Val Leu Gly Leu Leu Phe Leu Gly
225                 230                 235                 240

Ala Gly Leu Phe Ile Tyr Phe Arg Asn Gln Lys Gly Gln Ser Gly Leu
```

```
                    245                 250                 255

Gln Pro Thr Gly Leu Leu Ser
            260

<210> SEQ ID NO 16
<211> LENGTH: 142
<212> TYPE: PRT
<213> ORGANISM: Homo sapiens

<400> SEQUENCE: 16

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140

<210> SEQ ID NO 17
<211> LENGTH: 177
<212> TYPE: PRT
<213> ORGANISM: Homo sapiens

<400> SEQUENCE: 17

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
```

Phe

<210> SEQ ID NO 18
<211> LENGTH: 178
<212> TYPE: PRT
<213> ORGANISM: Homo sapiens

<400> SEQUENCE: 18

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 19
<211> LENGTH: 153
<212> TYPE: PRT
<213> ORGANISM: Homo sapiens

<400> SEQUENCE: 19

Ser Gln Pro His Thr Lys Pro Ser Val Phe Val Met Lys Asn Gly Thr
1               5                   10                  15

Asn Val Ala Cys Leu Val Lys Glu Phe Tyr Pro Lys Asp Ile Arg Ile
            20                  25                  30

Asn Leu Val Ser Ser Lys Lys Ile Thr Glu Phe Asp Pro Ala Ile Val
        35                  40                  45

Ile Ser Pro Ser Gly Lys Tyr Asn Ala Val Lys Leu Gly Lys Tyr Glu
    50                  55                  60

Asp Ser Asn Ser Val Thr Cys Ser Val Gln His Asp Asn Lys Thr Val
65                  70                  75                  80

His Ser Thr Asp Phe Glu Val Lys Thr Asp Ser Thr Asp His Val Lys
                85                  90                  95

Pro Lys Glu Thr Glu Asn Thr Lys Gln Pro Ser Lys Ser Cys His Lys
            100                 105                 110

Pro Lys Ala Ile Val His Thr Glu Lys Val Asn Met Met Ser Leu Thr
        115                 120                 125

```
Val Leu Gly Leu Arg Met Leu Phe Ala Lys Thr Val Ala Val Asn Phe
130                 135                 140

Leu Leu Thr Ala Lys Leu Phe Phe Leu
145                 150
```

<210> SEQ ID NO 20
<211> LENGTH: 173
<212> TYPE: PRT
<213> ORGANISM: Homo sapiens

<400> SEQUENCE: 20

```
Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
                20                  25                  30

Leu Leu Glu Lys Phe Phe Pro Asp Val Ile Lys Ile His Trp Gln Glu
            35                  40                  45

Lys Lys Ser Asn Thr Ile Leu Gly Ser Gln Glu Gly Asn Thr Met Lys
        50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170
```

<210> SEQ ID NO 21
<211> LENGTH: 189
<212> TYPE: PRT
<213> ORGANISM: Homo sapiens

<400> SEQUENCE: 21

```
Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
                20                  25                  30

Leu Leu Glu Lys Phe Phe Pro Asp Ile Ile Lys Ile His Trp Gln Glu
            35                  40                  45

Lys Lys Ser Asn Thr Ile Leu Gly Ser Gln Glu Gly Asn Thr Met Lys
        50                  55                  60

Thr Asn Asp Thr Tyr Met Lys Phe Ser Trp Leu Thr Val Pro Glu Glu
65                  70                  75                  80

Ser Leu Asp Lys Glu His Arg Cys Ile Val Arg His Glu Asn Asn Lys
                85                  90                  95

Asn Gly Ile Asp Gln Glu Ile Ile Phe Pro Pro Ile Lys Thr Asp Val
            100                 105                 110

Thr Thr Val Asp Pro Lys Asp Ser Tyr Ser Lys Asp Ala Asn Asp Val
        115                 120                 125
```

```
Ile Thr Met Asp Pro Lys Asp Asn Trp Ser Lys Asp Ala Asn Asp Thr
        130                 135                 140

Leu Leu Leu Gln Leu Thr Asn Thr Ser Ala Tyr Tyr Met Tyr Leu Leu
145                 150                 155                 160

Leu Leu Leu Lys Ser Val Val Tyr Phe Ala Ile Ile Thr Cys Cys Leu
                165                 170                 175

Leu Gly Arg Thr Ala Phe Cys Cys Asn Gly Glu Lys Ser
                180                 185
```

<210> SEQ ID NO 22
<211> LENGTH: 138
<212> TYPE: PRT
<213> ORGANISM: Mus musculus

<400> SEQUENCE: 22

```
Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
                20                  25                  30

Ile Asn Val Pro Lys Thr Met Glu Ser Gly Thr Phe Ile Thr Asp Lys
                35                  40                  45

Thr Val Leu Asp Met Lys Ala Met Asp Ser Lys Ser Asn Gly Ala Ile
50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro Cys Asp Ala Thr Leu
                85                  90                  95

Thr Glu Lys Ser Phe Glu Thr Asp Met Asn Leu Asn Phe Gln Asn Leu
                100                 105                 110

Ser Val Met Gly Leu Arg Ile Leu Leu Leu Lys Val Ala Gly Phe Asn
                115                 120                 125

Leu Leu Met Thr Leu Arg Leu Trp Ser Ser
                130                 135
```

<210> SEQ ID NO 23
<211> LENGTH: 173
<212> TYPE: PRT
<213> ORGANISM: Mus musculus

<400> SEQUENCE: 23

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
                35                  40                  45

Gly Lys Glu Val His Ser Gly Val Ser Thr Asp Pro Gln Ala Tyr Lys
50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
                115                 120                 125
```

```
Ile Thr Ser Ala Ser Tyr Gln Gln Gly Val Leu Ser Ala Thr Ile Leu
            130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 24
<211> LENGTH: 173
<212> TYPE: PRT
<213> ORGANISM: Mus musculus

<400> SEQUENCE: 24

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Ser Thr Asp Pro Gln Ala Tyr Lys
        50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
            130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170
```

<210> SEQ ID NO 25
<211> LENGTH: 167
<212> TYPE: PRT
<213> ORGANISM: Mus musculus

<400> SEQUENCE: 25

```
Asp Lys Arg Leu Asp Ala Asp Ile Ser Pro Lys Pro Thr Ile Phe Leu
1               5                   10                  15

Pro Ser Val Ala Glu Thr Asn Leu His Lys Thr Gly Thr Tyr Leu Cys
                20                  25                  30

Leu Leu Glu Lys Phe Phe Pro Asp Val Ile Arg Val Tyr Trp Lys Glu
            35                  40                  45

Lys Asn Gly Asn Thr Ile Leu Asp Ser Gln Glu Gly Asp Thr Leu Lys
        50                  55                  60

Thr Lys Gly Thr Tyr Met Lys Phe Ser Trp Leu Thr Val Pro Glu Arg
65                  70                  75                  80

Ala Met Gly Lys Glu His Ser Cys Ile Val Lys His Glu Asn Asn Lys
                85                  90                  95

Gly Gly Ala Asp Gln Glu Ile Phe Phe Pro Ser Ile Lys Lys Val Ala
            100                 105                 110
```

```
Thr Thr Cys Trp Gln Asp Lys Asn Asp Val Leu Gln Phe Gln Phe Thr
        115                 120                 125

Ser Thr Ser Ala Tyr Tyr Thr Tyr Leu Leu Leu Leu Lys Ser Val
130                 135                 140

Ile Tyr Leu Ala Ile Ile Ser Phe Ser Leu Leu Arg Arg Thr Ser Val
145                 150                 155                 160

Cys Gly Asn Glu Lys Lys Ser
                165

<210> SEQ ID NO 26
<211> LENGTH: 172
<212> TYPE: PRT
<213> ORGANISM: Mus musculus

<400> SEQUENCE: 26

Asp Lys Lys Leu Asp Ala Asp Ile Ser Pro Lys Pro Thr Ile Phe Leu
1               5                   10                  15

Pro Ser Val Ala Glu Thr Asn Leu His Lys Thr Gly Thr Tyr Leu Cys
                20                  25                  30

Val Leu Glu Lys Phe Phe Pro Asp Val Ile Arg Val Tyr Trp Lys Glu
            35                  40                  45

Lys Lys Gly Asn Thr Ile Leu Asp Ser Gln Glu Gly Asp Met Leu Lys
        50                  55                  60

Thr Asn Asp Thr Tyr Met Lys Phe Ser Trp Leu Thr Val Pro Glu Arg
65                  70                  75                  80

Ser Met Gly Lys Glu His Arg Cys Ile Val Lys His Glu Asn Asn Lys
                85                  90                  95

Gly Gly Ala Asp Gln Glu Ile Phe Phe Pro Thr Ile Lys Lys Val Ala
            100                 105                 110

Val Ser Thr Lys Pro Thr Thr Cys Trp Gln Asp Lys Asn Asp Val Leu
        115                 120                 125

Gln Leu Gln Phe Thr Ile Thr Ser Ala Tyr Tyr Thr Tyr Leu Leu Leu
    130                 135                 140

Leu Leu Lys Ser Val Ile Tyr Leu Ala Ile Ile Ser Phe Ser Leu Leu
145                 150                 155                 160

Arg Arg Thr Ser Val Cys Cys Asn Glu Lys Lys Ser
                165                 170

<210> SEQ ID NO 27
<211> LENGTH: 169
<212> TYPE: PRT
<213> ORGANISM: Mus musculus

<400> SEQUENCE: 27

Pro Ser Asp Lys Arg Leu Asp Ala Asp Ile Ser Pro Lys Pro Thr Ile
1               5                   10                  15

Phe Leu Pro Ser Val Ala Glu Thr Asn Leu His Lys Thr Gly Thr Tyr
                20                  25                  30

Leu Cys Ile Leu Glu Lys Phe Phe Pro Asp Val Ile Arg Val Tyr Trp
            35                  40                  45

Lys Asp Lys Asn Gly Asn Thr Ile Leu Asp Ser Gln Glu Gly Asp Thr
        50                  55                  60

Leu Lys Thr Lys Gly Thr Tyr Met Lys Phe Ser Trp Leu Thr Val Pro
65                  70                  75                  80

Glu Arg Ser Met Gly Lys Glu His Arg Cys Ile Val Lys His Glu Asn
                85                  90                  95
```

```
Asn Lys Gly Gly Ala Asp Gln Glu Ile Phe Phe Pro Ser Ile Lys Lys
                100                 105                 110

Val Ala Thr Thr Cys Trp Gln Asp Lys Asn Asp Val Leu Gln Leu Gln
            115                 120                 125

Phe Met Ser Thr Ser Ala Tyr Tyr Thr Tyr Leu Leu Leu Leu Leu Lys
        130                 135                 140

Ser Val Ile Tyr Leu Ala Ile Ile Ser Phe Ser Leu Leu Arg Arg Thr
145                 150                 155                 160

Ser Val Cys Cys Asn Glu Lys Arg Ser
                165
```

<210> SEQ ID NO 28
<211> LENGTH: 190
<212> TYPE: PRT
<213> ORGANISM: Mus musculus

<400> SEQUENCE: 28

```
Asp Lys Arg Thr Asp Ser Asp Phe Ser Pro Lys Pro Thr Ile Phe Leu
1               5                   10                  15

Pro Ser Ala Ala Glu Thr Asn Leu His Lys Ala Gly Thr Tyr Leu Cys
            20                  25                  30

Leu Leu Glu Lys Phe Phe Pro Lys Val Ile Arg Val Tyr Trp Lys Glu
        35                  40                  45

Lys Asp Gly Glu Lys Ile Leu Glu Ser Gln Gly Asn Thr Ile Lys
50                  55                  60

Thr Asn Asp Arg Tyr Met Lys Phe Ser Trp Leu Thr Val Thr Glu Asp
65                  70                  75                  80

Ser Met Ala Lys Glu His Ser Cys Ile Val Lys His Glu Asn Asn Lys
                85                  90                  95

Arg Gly Val Asp Gln Glu Ile Leu Phe Pro Pro Ile Gly Lys Ala Phe
            100                 105                 110

Thr Thr Ile Asn Val Asn Pro Arg Asp Ser Val Leu Arg His Glu Asn
        115                 120                 125

Val Asn Asn Ala Thr Asp Leu Glu Asp Cys Met Lys Gly Arg Lys Asp
130                 135                 140

Met Leu Gln Leu Gln Val Thr Thr Tyr Ala Phe Tyr Thr Tyr Leu
145                 150                 155                 160

Ile Leu Phe Phe Lys Ser Met Val His Leu Ala Phe Val Phe Cys
                165                 170                 175

Leu Phe Arg Arg Ala Ala Met Ser Cys Asp Asp Gln Arg Ser
            180                 185                 190
```

<210> SEQ ID NO 29
<211> LENGTH: 16
<212> TYPE: PRT
<213> ORGANISM: Manduca sexta

<400> SEQUENCE: 29

```
Ala Asn Glu Arg Ala Asp Leu Ile Ala Tyr Leu Lys Gln Ala Thr Lys
1               5                   10                  15
```

<210> SEQ ID NO 30
<211> LENGTH: 263
<212> TYPE: PRT
<213> ORGANISM: Artificial Sequence
<220> FEATURE:
<223> OTHER INFORMATION: Synthetic sequence comprising a MHC portion and a TCR portion

<400> SEQUENCE: 30

```
Met Ala Thr Ile Gly Ala Leu Leu Arg Phe Phe Ile Ala Val
1               5                   10                  15

Leu Met Ser Ser Gln Lys Ser Trp Ala Ile Lys Glu Glu His Thr Ile
            20                  25                  30

Ile Gln Ala Glu Phe Tyr Leu Pro Asp Lys Arg Gly Glu Phe Met
        35                  40                  45

Phe Asp Phe Asp Gly Asp Glu Ile Phe His Val Asp Ile Glu Lys Ser
    50                  55                  60

Glu Thr Ile Trp Arg Leu Glu Glu Phe Ala Lys Phe Ala Ser Phe Glu
65                  70                  75                  80

Ala Gln Gly Ala Leu Ala Asn Ile Ala Val Asp Lys Ala Asn Leu Asp
                85                  90                  95

Val Met Lys Glu Arg Ser Asn Asn Thr Pro Asp Ala Asn Val Ala Pro
            100                 105                 110

Glu Val Thr Val Leu Ser Arg Ser Pro Val Asn Leu Gly Glu Pro Asn
            115                 120                 125

Ile Leu Ile Cys Phe Ile Asp Lys Phe Ser Pro Pro Val Val Asn Val
    130                 135                 140

Thr Trp Phe Arg Asn Gly Arg Pro Val Thr Glu Gly Val Ser Glu Thr
145                 150                 155                 160

Val Phe Leu Pro Arg Asp Asp His Leu Phe Arg Lys Phe His Tyr Leu
                165                 170                 175

Thr Phe Leu Pro Ser Thr Asp Asp Phe Tyr Asp Cys Glu Val Asp His
            180                 185                 190

Trp Gly Leu Glu Glu Pro Leu Arg Lys His Trp Glu Phe Glu Glu Lys
        195                 200                 205

Thr Leu Leu Pro Glu Thr Lys Glu Cys Asp Ala Thr Leu Thr Glu Lys
            210                 215                 220

Ser Phe Glu Thr Asp Met Asn Leu Asn Phe Gln Asn Leu Ser Val Met
225                 230                 235                 240

Gly Leu Arg Ile Leu Leu Leu Lys Val Ala Gly Phe Asn Leu Leu Met
                245                 250                 255

Thr Leu Arg Leu Trp Ser Ser
            260
```

<210> SEQ ID NO 31
<211> LENGTH: 315
<212> TYPE: PRT
<213> ORGANISM: Artificial Sequence
<220> FEATURE:
<223> OTHER INFORMATION: Synthetic sequence comprising a MHC portion and a TCR portion

<400> SEQUENCE: 31

```
Met Val Trp Leu Pro Arg Val Pro Cys Val Ala Ala Val Ile Leu Leu
1               5                   10                  15

Leu Thr Val Leu Ser Pro Pro Val Ala Leu Val Arg Asp Ser Gly Ser
            20                  25                  30

Ala Asn Glu Arg Ala Asp Leu Ile Ala Tyr Leu Lys Gln Ala Thr Lys
        35                  40                  45

Glu Phe Arg Ser Gly Gly Gly Gly Ser Leu Val Pro Arg Gly Ser Gly
    50                  55                  60

Gly Gly Gly Ser Val Asp Arg Pro Trp Phe Leu Glu Tyr Cys Lys Ser
65                  70                  75                  80
```

Glu Cys His Phe Tyr Asn Gly Thr Gln Arg Val Arg Leu Leu Val Arg
                85                  90                  95

Tyr Phe Tyr Asn Leu Glu Glu Asn Leu Arg Phe Asp Ser Asp Val Gly
            100                 105                 110

Glu Phe Arg Ala Val Thr Glu Leu Gly Arg Pro Asp Ala Glu Asn Trp
        115                 120                 125

Asn Ser Gln Pro Glu Phe Leu Glu Gln Lys Arg Ala Glu Val Asp Thr
    130                 135                 140

Val Cys Arg His Asn Tyr Glu Ile Phe Asp Asn Phe Leu Val Pro Arg
145                 150                 155                 160

Arg Val Glu Pro Thr Val Thr Val Tyr Pro Thr Lys Thr Gln Pro Leu
                165                 170                 175

Glu His His Asn Leu Leu Val Cys Ser Val Ser Asp Phe Tyr Pro Gly
            180                 185                 190

Asn Ile Glu Val Arg Trp Phe Arg Asn Gly Lys Glu Glu Lys Thr Gly
        195                 200                 205

Ile Val Ser Thr Gly Leu Val Arg Asn Gly Asp Trp Thr Phe Gln Thr
    210                 215                 220

Leu Val Met Leu Glu Thr Val Pro Gln Ser Gly Glu Val Tyr Thr Cys
225                 230                 235                 240

Gln Val Glu His Pro Ser Leu Thr Asp Pro Val Thr Val Glu Trp Lys
                245                 250                 255

Ala Gln Ser Thr Ser Ala Gln Asn Lys Cys Gly Ile Thr Ser Ala Ser
            260                 265                 270

Tyr His Gln Gly Val Leu Ser Ala Thr Ile Leu Tyr Glu Ile Leu Leu
        275                 280                 285

Gly Lys Ala Thr Leu Tyr Ala Val Leu Val Ser Gly Leu Val Leu Met
    290                 295                 300

Ala Met Val Lys Lys Lys Asn Ser Ala Ala Ala
305                 310                 315

<210> SEQ ID NO 32
<211> LENGTH: 312
<212> TYPE: PRT
<213> ORGANISM: Artificial Sequence
<220> FEATURE:
<223> OTHER INFORMATION: Synthetic sequence comprising a MHC portion and
      a TCR portion

<400> SEQUENCE: 32

Met Val Trp Leu Pro Arg Val Pro Cys Val Ala Ala Val Ile Leu Leu
1               5                   10                  15

Leu Thr Val Leu Ser Pro Pro Val Ala Leu Val Arg Asp Ser Gly Ser
            20                  25                  30

Gly Lys Lys Val Ile Thr Ala Phe Asn Glu Gly Leu Lys Glu Phe Arg
        35                  40                  45

Ser Gly Gly Gly Gly Ser Leu Val Pro Arg Gly Ser Gly Gly Gly Gly
    50                  55                  60

Ser Val Asp Arg Pro Trp Phe Leu Glu Tyr Cys Lys Ser Glu Cys His
65                  70                  75                  80

Phe Tyr Asn Gly Thr Gln Arg Val Arg Leu Leu Val Arg Tyr Phe Tyr
                85                  90                  95

Asn Leu Glu Glu Asn Leu Arg Phe Asp Ser Asp Val Gly Glu Phe Arg
            100                 105                 110

Ala Val Thr Glu Leu Gly Arg Pro Asp Ala Glu Asn Trp Asn Ser Gln
        115                 120                 125

```
Pro Glu Phe Leu Glu Gln Lys Arg Ala Glu Val Asp Thr Val Cys Arg
            130                 135                 140

His Asn Tyr Glu Ile Phe Asp Asn Phe Leu Val Pro Arg Arg Val Glu
145                 150                 155                 160

Pro Thr Val Thr Val Tyr Pro Thr Lys Thr Gln Pro Leu Glu His His
                165                 170                 175

Asn Leu Leu Val Cys Ser Val Ser Asp Phe Tyr Pro Gly Asn Ile Glu
            180                 185                 190

Val Arg Trp Phe Arg Asn Gly Lys Glu Glu Lys Thr Gly Ile Val Ser
            195                 200                 205

Thr Gly Leu Val Arg Asn Gly Asp Trp Thr Phe Gln Thr Leu Val Met
210                 215                 220

Leu Glu Thr Val Pro Gln Ser Gly Glu Val Tyr Thr Cys Gln Val Glu
225                 230                 235                 240

His Pro Ser Leu Thr Asp Pro Val Thr Val Glu Trp Lys Ala Gln Ser
                245                 250                 255

Thr Ser Ala Gln Asn Lys Cys Gly Ile Thr Ser Ala Ser Tyr His Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Gly Leu Val Leu Met Ala Met Val
290                 295                 300

Lys Lys Lys Asn Ser Ala Ala Ala
305                 310
```

<210> SEQ ID NO 33
<211> LENGTH: 797
<212> TYPE: PRT
<213> ORGANISM: Artificial Sequence
<220> FEATURE:
<223> OTHER INFORMATION: Synthetic peptide comprising a fusion of CD80 and Lck

<400> SEQUENCE: 33

```
Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
                35                  40                  45

Lys Val Leu Leu Pro Cys Arg Tyr Asn Ser Pro His Glu Asp Glu Ser
50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
            130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
```

```
              165                 170                 175
Ser Trp Leu Glu Asn Gly Arg Glu Leu Pro Gly Ile Asn Thr Thr Ile
            180                 185                 190
Ser Gln Asp Pro Glu Ser Glu Leu Tyr Thr Ile Ser Ser Gln Leu Asp
            195                 200                 205
Phe Asn Thr Thr Arg Asn His Thr Ile Lys Cys Leu Ile Lys Tyr Gly
            210                 215                 220
Asp Ala His Val Ser Glu Asp Phe Thr Trp Glu Lys Pro Pro Glu Asp
225                 230                 235                 240
Pro Pro Asp Ser Lys Asn Thr Leu Val Leu Phe Gly Ala Gly Phe Gly
                245                 250                 255
Ala Val Ile Thr Val Val Ile Val Val Ile Ile Lys Cys Phe Cys
                260                 265                 270
Lys His Arg Ser Cys Phe Arg Arg Asn Glu Ala Ser Arg Glu Thr Asn
                275                 280                 285
Asn Ser Leu Thr Phe Gly Pro Glu Glu Ala Leu Ala Glu Gln Thr Val
            290                 295                 300
Phe Leu Thr Thr Ser His Tyr Pro Ile Val Pro Leu Asp Ser Lys Ile
305                 310                 315                 320
Ser Leu Pro Ile Arg Asn Gly Ser Glu Val Arg Asp Pro Leu Val Thr
                325                 330                 335
Tyr Glu Gly Ser Leu Pro Pro Ala Ser Pro Leu Gln Asp Asn Leu Val
            340                 345                 350
Ile Ala Leu His Ser Tyr Glu Pro Ser His Asp Gly Asp Leu Gly Phe
            355                 360                 365
Glu Lys Gly Glu Gln Leu Arg Ile Leu Glu Gln Ser Gly Glu Trp Trp
            370                 375                 380
Lys Ala Gln Ser Leu Thr Thr Gly Gln Glu Gly Phe Ile Pro Phe Asn
385                 390                 395                 400
Phe Val Ala Lys Ala Asn Ser Leu Glu Pro Glu Pro Trp Phe Phe Lys
                405                 410                 415
Asn Leu Ser Arg Lys Asp Ala Glu Arg Gln Leu Leu Ala Pro Gly Asn
                420                 425                 430
Thr His Gly Ser Phe Leu Ile Arg Glu Ser Glu Ser Thr Ala Gly Ser
            435                 440                 445
Phe Ser Leu Ser Val Arg Asp Phe Asp Gln Asn Gln Gly Glu Val Val
            450                 455                 460
Lys His Tyr Lys Ile Arg Asn Leu Asp Asn Gly Gly Phe Tyr Ile Ser
465                 470                 475                 480
Pro Arg Ile Thr Phe Pro Gly Leu His Asp Leu Val Arg His Tyr Thr
                485                 490                 495
Asn Ala Ser Asp Gly Leu Cys Thr Lys Leu Ser Arg Pro Cys Gln Thr
                500                 505                 510
Gln Lys Pro Gln Lys Pro Trp Trp Glu Asp Glu Trp Glu Val Pro Arg
                515                 520                 525
Glu Thr Leu Lys Leu Val Glu Arg Leu Gly Ala Gly Gln Phe Gly Glu
            530                 535                 540
Val Trp Met Gly Tyr Tyr Asn Gly His Thr Lys Val Ala Val Lys Ser
545                 550                 555                 560
Leu Lys Gln Gly Ser Met Ser Pro Asp Ala Phe Leu Ala Glu Ala Asn
                565                 570                 575
Leu Met Lys Gln Leu Gln His Pro Arg Leu Val Arg Leu Tyr Ala Val
                580                 585                 590
```

Val Thr Gln Glu Pro Ile Tyr Ile Thr Glu Tyr Met Glu Asn Gly
        595                 600                 605

Ser Leu Val Asp Phe Leu Lys Thr Pro Ser Gly Ile Lys Leu Asn Val
610                 615                 620

Asn Lys Leu Leu Asp Met Ala Ala Gln Ile Ala Glu Gly Met Ala Phe
625                 630                 635                 640

Ile Glu Glu Gln Asn Tyr Ile His Arg Asp Leu Arg Ala Ala Asn Ile
                645                 650                 655

Leu Val Ser Asp Thr Leu Ser Cys Lys Ile Ala Asp Phe Gly Leu Ala
                660                 665                 670

Arg Leu Ile Glu Asp Asn Glu Tyr Thr Ala Arg Glu Gly Ala Lys Phe
                675                 680                 685

Pro Ile Lys Trp Thr Ala Pro Glu Ala Ile Asn Tyr Gly Thr Phe Thr
                690                 695                 700

Ile Lys Ser Asp Val Trp Ser Phe Gly Ile Leu Leu Thr Glu Ile Val
705                 710                 715                 720

Thr His Gly Arg Ile Pro Tyr Pro Gly Met Thr Asn Pro Glu Val Ile
                725                 730                 735

Gln Asn Leu Glu Arg Gly Tyr Arg Met Val Arg Pro Asp Asn Cys Pro
                740                 745                 750

Glu Glu Leu Tyr His Leu Met Met Leu Cys Trp Lys Glu Arg Pro Glu
                755                 760                 765

Asp Arg Pro Thr Phe Asp Tyr Leu Arg Ser Val Leu Asp Asp Phe Phe
                770                 775                 780

Thr Ala Thr Glu Gly Gln Tyr Gln Pro Gln Pro Gly Thr
785                 790                 795

<210> SEQ ID NO 34
<211> LENGTH: 800
<212> TYPE: PRT
<213> ORGANISM: Artificial Sequence
<220> FEATURE:
<223> OTHER INFORMATION: Synthetic peptide comprising a fusion of CD86
      and Lck

<400> SEQUENCE: 34

Met Asp Pro Arg Cys Thr Met Gly Leu Ala Ile Leu Ile Phe Val Thr
1               5                   10                  15

Val Leu Leu Ile Ser Asp Ala Val Ser Val Glu Thr Gln Ala Tyr Phe
                20                  25                  30

Asn Gly Thr Ala Tyr Leu Pro Cys Pro Phe Thr Lys Ala Gln Asn Ile
                35                  40                  45

Ser Leu Ser Glu Leu Val Val Phe Trp Gln Asp Gln Gln Lys Leu Val
50                  55                  60

Leu Tyr Glu His Tyr Leu Gly Thr Glu Lys Leu Asp Ser Val Asn Ala
65                  70                  75                  80

Lys Tyr Leu Gly Arg Thr Ser Phe Asp Arg Asn Asn Trp Thr Leu Arg
                85                  90                  95

Leu His Asn Val Gln Ile Lys Asp Met Gly Ser Tyr Asp Cys Phe Ile
                100                 105                 110

Gln Lys Lys Pro Pro Thr Gly Ser Ile Ile Leu Gln Gln Thr Leu Thr
                115                 120                 125

Glu Leu Ser Val Ile Ala Asn Phe Ser Glu Pro Glu Ile Lys Leu Ala
                130                 135                 140

Gln Asn Val Thr Gly Asn Ser Gly Ile Asn Leu Thr Cys Thr Ser Lys

-continued

```
            145                 150                 155                 160
        Gln Gly His Pro Lys Pro Lys Met Tyr Phe Leu Ile Thr Asn Ser
                        165                 170                 175
        Thr Asn Glu Tyr Gly Asp Asn Met Gln Ile Ser Gln Asp Asn Val Thr
                        180                 185                 190
        Glu Leu Phe Ser Ile Ser Asn Ser Leu Ser Leu Ser Phe Pro Asp Gly
                        195                 200                 205
        Val Trp His Met Thr Val Val Cys Val Leu Glu Thr Glu Ser Met Lys
                210                 215                 220
        Ile Ser Ser Lys Pro Leu Asn Phe Thr Gln Glu Phe Pro Ser Pro Gln
        225                 230                 235                 240
        Thr Tyr Trp Lys Glu Ile Thr Ala Ser Val Thr Val Ala Leu Leu Leu
                            245                 250                 255
        Val Met Leu Leu Ile Ile Val Cys His Lys Lys Pro Asn Gln Pro Ser
                        260                 265                 270
        Arg Pro Ser Asn Thr Ala Ser Lys Leu Glu Arg Asp Ser Asn Ala Asp
                        275                 280                 285
        Arg Glu Thr Ile Asn Leu Lys Glu Leu Glu Pro Gln Ile Ala Ser Ala
                290                 295                 300
        Lys Pro Asn Ala Glu Cys Thr Ser His Tyr Pro Ile Val Pro Leu Asp
        305                 310                 315                 320
        Ser Lys Ile Ser Leu Pro Ile Arg Asn Gly Ser Glu Val Arg Asp Pro
                        325                 330                 335
        Leu Val Thr Tyr Glu Gly Ser Leu Pro Pro Ala Ser Pro Leu Gln Asp
                        340                 345                 350
        Asn Leu Val Ile Ala Leu His Ser Tyr Glu Pro Ser His Asp Gly Asp
                        355                 360                 365
        Leu Gly Phe Glu Lys Gly Glu Gln Leu Arg Ile Leu Glu Gln Ser Gly
                        370                 375                 380
        Glu Trp Trp Lys Ala Gln Ser Leu Thr Thr Gly Gln Glu Gly Phe Ile
        385                 390                 395                 400
        Pro Phe Asn Phe Val Ala Lys Ala Asn Ser Leu Glu Pro Glu Pro Trp
                        405                 410                 415
        Phe Phe Lys Asn Leu Ser Arg Lys Asp Ala Glu Arg Gln Leu Leu Ala
                        420                 425                 430
        Pro Gly Asn Thr His Gly Ser Phe Leu Ile Arg Glu Ser Glu Ser Thr
                        435                 440                 445
        Ala Gly Ser Phe Ser Leu Ser Val Arg Asp Phe Asp Gln Asn Gln Gly
                450                 455                 460
        Glu Val Val Lys His Tyr Lys Ile Arg Asn Leu Asp Asn Gly Gly Phe
        465                 470                 475                 480
        Tyr Ile Ser Pro Arg Ile Thr Phe Pro Gly Leu His Asp Leu Val Arg
                        485                 490                 495
        His Tyr Thr Asn Ala Ser Asp Gly Leu Cys Thr Lys Leu Ser Arg Pro
                        500                 505                 510
        Cys Gln Thr Gln Lys Pro Gln Lys Pro Trp Trp Glu Asp Glu Trp Glu
                    515                 520                 525
        Val Pro Arg Glu Thr Leu Lys Leu Val Glu Arg Leu Gly Ala Gly Gln
                530                 535                 540
        Phe Gly Glu Val Trp Met Gly Tyr Tyr Asn Gly His Thr Lys Val Ala
        545                 550                 555                 560
        Val Lys Ser Leu Lys Gln Gly Ser Met Ser Pro Asp Ala Phe Leu Ala
                        565                 570                 575
```

Glu Ala Asn Leu Met Lys Gln Leu Gln His Pro Arg Leu Val Arg Leu
            580                 585                 590

Tyr Ala Val Val Thr Gln Pro Ile Tyr Ile Ile Thr Glu Tyr Met
        595                 600                 605

Glu Asn Gly Ser Leu Val Asp Phe Leu Lys Thr Pro Ser Gly Ile Lys
610                 615                 620

Leu Asn Val Asn Lys Leu Leu Asp Met Ala Ala Gln Ile Ala Glu Gly
625                 630                 635                 640

Met Ala Phe Ile Glu Glu Gln Asn Tyr Ile His Arg Asp Leu Arg Ala
            645                 650                 655

Ala Asn Ile Leu Val Ser Asp Thr Leu Ser Cys Lys Ile Ala Asp Phe
            660                 665                 670

Gly Leu Ala Arg Leu Ile Glu Asp Asn Glu Tyr Thr Ala Arg Glu Gly
            675                 680                 685

Ala Lys Phe Pro Ile Lys Trp Thr Ala Pro Glu Ala Ile Asn Tyr Gly
            690                 695                 700

Thr Phe Thr Ile Lys Ser Asp Val Trp Ser Phe Gly Ile Leu Leu Thr
705                 710                 715                 720

Glu Ile Val Thr His Gly Arg Ile Pro Tyr Pro Gly Met Thr Asn Pro
            725                 730                 735

Glu Val Ile Gln Asn Leu Glu Arg Gly Tyr Arg Met Val Arg Pro Asp
            740                 745                 750

Asn Cys Pro Glu Glu Leu Tyr His Leu Met Met Leu Cys Trp Lys Glu
            755                 760                 765

Arg Pro Glu Asp Arg Pro Thr Phe Asp Tyr Leu Arg Ser Val Leu Asp
            770                 775                 780

Asp Phe Phe Thr Ala Thr Glu Gly Gln Tyr Gln Pro Gln Pro Gly Thr
785                 790                 795                 800

<210> SEQ ID NO 35
<211> LENGTH: 824
<212> TYPE: DNA
<213> ORGANISM: Artificial Sequence
<220> FEATURE:
<223> OTHER INFORMATION: Nucleotide sequence for synthetic peptide
      comprising an MHC portion and a TCR portion (see SEQ ID NO: 30)

<400> SEQUENCE: 35
aataagcttc tcgagcgcca ccatggccac aattggagcc ctgctgttaa gattttctt      60 cattgctgtt ctgatgagct cccagaagtc atgggctatc aaagaggaac acaccatcat    120
ccaggcggag ttctatcttt accagacaa cgtggagag tttatgtttg actttgacgg      180
cgatgagatt ttccatgtag acattgaaaa gtcagagacc atctggagac ttgaagaatt    240
tgcaaagttt gccagctttg aggctcaggg tgcactggct aatatagctg ggacaaagc     300 taacctggat gtcatgaaag agcgttccaa caacactcca gatgccaacg tggccccaga    360
ggtgactgta ctctccagaa gccctgtgaa cctgggagag cccaacatcc tcatctgttt    420
cattgacaag ttctcccctc cagtggtcaa tgtcacctgg ttccggaatg acggcctgt     480 caccgaaggc gtgtcagaga cagtgtttct cccgagggac gatcacctct ccgcaaattt    540
ccactatctg accttcctgc cctccacaga tgatttctat gactgtgagg tggatcactg    600
gggtttggag gagcctctgc ggaagcactg ggagtttgaa gagaaaccc tcctcccaga    660 aactaaagag tgtgatgcca cgttgaccga gaaaagcttt gaaacagata tgaacctaaa    720 cttttcaaaac ctgtcagtta tgggactccg aatcctcctg ctgaaagtag cgggatttaa    780

```
cctgctcatg acgctgaggc tgtggtccag ttgaggatcc gcta              824
```

<210> SEQ ID NO 36
<211> LENGTH: 988
<212> TYPE: DNA
<213> ORGANISM: Artificial Sequence
<220> FEATURE:
<223> OTHER INFORMATION: Nucleotide sequence for synthetic peptide
      comprising an MHC portion and a TCR portion (see SEQ ID NO: 31)

<400> SEQUENCE: 36

```
aatctcgagc gccaccatgg tgtggctccc cagagttccc tgtgtggcag ctgtgatcct   60
gttgctgaca gtgctgagcc ctccagtggc tttggtcaga gactccggat ccgccaacga  120
gagggccgac ctgatcgcct acctgaagca ggccaccaag gaattcagat ccggaggcgg  180
aggctccctg gtgcctcggg gctccggagg cggaggctcc gtcgacagac catggttttt  240
ggaatactgt aaatctgagt gtcatttcta caacgggacg cagcgcgtgc ggcttctggt  300
aagatacttc tacaacctgg aggagaacct gcgcttcgac agcgacgtgg gcgagttccg  360
cgcggtgacc gagctggggc ggccagacgc cgagaactgg aacagccagc cggagttcct  420
ggagcaaaag cgggccgagg tggacacggt gtgcagacac aactatgaga tcttcgataa  480
cttccttgtg ccgcggagag ttgagcctac ggtgactgtg taccccacaa agacgcagcc  540
cctggaacac cacaacctcc tggtctgctc tgtgagtgac ttctaccctg caacattga   600
agtcagatgg ttccggaatg gcaaggagga gaaaacagga attgtgtcca cgggcctggt  660
ccgaaatgga gactggacct tccagacact ggtgatgctg agacggttc  ctcagagtgg  720
agaggtttac acctgccagg tggagcatcc cagcctgacc gaccctgtca cggtcgagtg  780
gaaagcacag tccacatctg cacagaacaa gtgtggaatc actagtgcat cctatcatca  840
gggggttctg tctgcaacca tcctctatga tcctactg    ggaaggcca  cctatatgc   900
tgtgctggtc agtggcctag tgctgatggc catggtcaag aaaaaaatt  ccgcggccgc  960
atgatgagat ctgagctcca tagaggcg                                    988
```

<210> SEQ ID NO 37
<211> LENGTH: 979
<212> TYPE: DNA
<213> ORGANISM: Artificial Sequence
<220> FEATURE:
<223> OTHER INFORMATION: Nucleotide sequence for synthetic peptide
      comprising an MHC portion and a TCR portion (see SEQ ID NO: 32)

<400> SEQUENCE: 37

```
aatctcgagc gccaccatgg tgtggctccc cagagttccc tgtgtggcag ctgtgatcct   60
gttgctgaca gtgctgagcc ctccagtggc tttggtcaga gactccggat ccggcaagaa  120
ggtgatcacc gccttcaacg agggcctgaa ggaattcaga tccggaggcg gaggctccct  180
ggtgcctcgg ggctccggag gcggaggctc cgtcgacaga ccatggtttt tggaatactg  240
taaatctgag tgtcatttct acaacgggac gcagcgcgtg cggcttctgg taagatactt  300
ctacaacctg gaggagaacc tgcgcttcga cagcgacgtg ggcgagttcc gcgcggtgac  360
cgagctgggg cggccagacg ccgagaactg aacagccag ccggagttcc tggagcaaaa  420
gcgggccgag gtggacacgg tgtgcagaca caactatgag atcttcgata acttccttgt  480
gccgcggaga gttgagccta cggtgactgt gtaccccaca aagacgcagc cctggaaca   540
ccacaacctc ctggtctgct ctgtgagtga cttctaccct gcaacattg  aagtcagatg  600
```

| | |
|---|---|
| gttccggaat ggcaaggagg agaaaacagg aattgtgtcc acgggcctgg tccgaaatgg | 660 |
| agactggacc ttccagacac tggtgatgct ggagacggtt cctcagagtg gagaggttta | 720 |
| cacctgccag gtggagcatc ccagcctgac cgaccctgtc acggtcgagt ggaaagcaca | 780 |
| gtccacatct gcacagaaca agtgtggaat cactagtgca tcctatcatc agggggttct | 840 |
| gtctgcaacc atcctctatg agatcctact ggggaaggcc acccctatatg ctgtgctggt | 900 |
| cagtggccta gtgctgatgg ccatggtcaa gaaaaaaaat tccgcggccg catgatgaga | 960 |
| tctgagctcc atagaggcg | 979 |

<210> SEQ ID NO 38
<211> LENGTH: 2433
<212> TYPE: DNA
<213> ORGANISM: Artificial Sequence
<220> FEATURE:
<223> OTHER INFORMATION: Nucleotide sequence for synthetic peptide comprising a fusion of CD80 and Lck (see SEQ ID NO: 33)

<400> SEQUENCE: 38

| | |
|---|---|
| acgtctagat acctcgaggc caccatggct tgcaattgtc agttgatgca ggatacacca | 60 |
| ctcctcaagt ttccatgtcc aaggctcatt cttctctttg tgctgctgat tcgtctttca | 120 |
| caagtgtctt cagatgttga tgaacaactg tccaagtcag tgaaagataa ggtattgctg | 180 |
| ccttgccgtt acaactctcc tcatgaagat gagtctgaag accgaatcta ctggcaaaaa | 240 |
| catgacaaag tggtgctgtc tgtcattgct gggaaactaa agtgtggcc cgagtataag | 300 |
| aaccggactt tatatgacaa cactacctac tctcttatca tcctgggcct ggtcctttca | 360 |
| gaccggggca catacagctg tgtcgttcaa aagaaggaaa gggaacgta tgaagttaaa | 420 |
| cacttggctt tagtaaagtt gtccatcaaa gctgacttct ctaccccaa cataactgag | 480 |
| tctggaaacc catctgcaga cactaaaagg attacctgct ttgcttccgg gggtttccca | 540 |
| aagcctcgct tctcttggtt ggaaaatgga agagaattac ctggcatcaa tacgacaatt | 600 |
| tcccaggatc ctgaatctga attgtacacc attagtagcc aactagattt caatacgact | 660 |
| cgcaaccaca ccattaagtg tctcattaaa tatggagatg ctcacgtgtc agaggacttc | 720 |
| acctgggaaa accccccaga agaccctcct gatagcaaga cacacttgt gctctttggg | 780 |
| gcaggattcg cgcagtaat aacagtcgtc gtcatcgttg tcatcatcaa atgcttctgt | 840 |
| aagcacagaa gctgtttcag aagaaatgag gcaagcagag aaacaaacaa cagccttacc | 900 |
| ttcgggcctg aagaagcatt agctgaacag accgtcttcc ttaccactag tcactatccc | 960 |
| atagtcccac tggacagcaa gatctcgctg cccatccgga atggctctga agtgcgggac | 1020 |
| ccactggtca cctatgaggg atctctccca ccagcatccc cgctgcaaga caacctggtt | 1080 |
| atcgccctgc acagttatga gccctcccat gatggagact gggcttttga agggtgaa | 1140 |
| cagctccgaa tcctggagca gagcggtgag tggtggaagg ctcagtccct gacgactggc | 1200 |
| caagaaggct tcattccctt caacttcgtg gcgaaagcaa acagcctgga gcctgaacct | 1260 |
| tggttcttca gaatctgag ccgtaaggac gccgagcggc agcttttggc gcccgggaac | 1320 |
| acgcatggat ccttcctgat ccgggaaagc gaaagcactg cggggtcctt ttccctgtcg | 1380 |
| gtcagagact tcgaccagaa ccaggagaa gtggtgaaac attacaagat ccgtaaccta | 1440 |
| gacaacggtg gcttctacat ctcccctcgt atcacttttc ccggattgca cgatctagtc | 1500 |
| cgccattaca ccaacgcctc tgatgggctg tgcacaaagt tgagccgtcc ttgccagacc | 1560 |
| cagaagcccc agaaaccatg gtgggaggac gaatgggaag ttcccaggga aacactgaag | 1620 |

```
ttggtggagc ggctgggagc tggccagttc ggggaagtgt ggatgggta ctacaacgga    1680 cacacgaagg tggcggtgaa gagtctgaaa caagggagca tgtcccccga cgccttcctg    1740
gctgaggcta acctcatgaa gcagctgcag cacccgcggc tagtccggct ttatgcagtg    1800
gtcacccagg aacccatcta catcatcacg aatacatgg agaacgggag cctagtagat    1860
tttctcaaga ctccctcggg catcaagttg aatgtcaaca aacttttgga catggcagcc    1920
cagattgcag agggcatggc gttcatcgaa gaacagaatt acatccatcg ggacctgcgc    1980
gccgccaaca tcctggtgtc tgacacgctg agctgcaaga ttgcagactt tggcctggcg    2040
cgcctcattg aggacaatga gtacacggcc cgggaggggg ccaaatttcc cattaagtgg    2100
acagcaccag aagccattaa ctatgggacc ttcaccatca agtcagacgt gtggtccttc    2160
gggatcttgc ttacagagat cgtcacccac ggtcgaatcc cttacccagg aatgaccaac    2220
cctgaagtca ttcagaacct ggagagaggc taccgcatgt gagacctga caactgtccg    2280 gaagagctgt accacctcat gatgctgtgc tggaaggagc gcccagagga ccggcccacg    2340
tttgactacc ttcggagtgt tctggatgac ttcttcacag ccacagaggg ccagtaccag    2400
ccccagcctg gtacctagtg agaattctac atg                                 2433
```

<210> SEQ ID NO 39
<211> LENGTH: 2442
<212> TYPE: DNA
<213> ORGANISM: Artificial Sequence
<220> FEATURE:
<223> OTHER INFORMATION: Nucleotide sequence for synthetic peptide
      comprising a fusion of CD86 and Lck (see SEQ ID NO: 34)

<400> SEQUENCE: 39

```
tactctagat acctcgaggc caccatggac cccagatgca ccatgggctt ggcaatcctt     60
atctttgtga cagtcttgct gatctcagat gctgtttccg tggagacgca agcttatttc    120
aatgggactg catatctgcc gtgcccattt acaaaggctc aaaacataag cctgagtgag    180
ctggtagtat tttggcagga ccagcaaaag ttggttctgt acgagcacta tttgggcaca    240
gagaaacttg atagtgtgaa tgccaagtac ctgggccgca cgagctttga caggaacaac    300
tggactctac gacttcacaa tgttcagatc aaggacatgg gctcgtatga ttgtttttata    360 caaaaaaagc cacccacagg atcaattatc ctccaacaga cattaacaga actgtcagtg    420
atcgccaact tcagtgaacc tgaaataaaa ctggctcaga atgtaacagg aaattctggc    480
ataaatttga cctgcacgtc taagcaaggt caccccgaaac ctaagaagat gtattttctg    540
ataactaatt caactaatga gtatggtgat aacatgcaga tatcacaaga taatgtcaca    600
gaactgttca gtatctccaa cagcctctct ctttcattcc cggatggtgt gtggcatatg    660
accgttgtgt gtgttctgga aacggagtca atgaagattt cctccaaacc tctcaatttc    720
actcaagagt ttccatctcc tcaaacgtat tggaaggaga ttacagcttc agttactgtg    780
gccctcctcc ttgtgatgct gctcatcatt gtatgtcaca agaagccgaa tcagcctagc    840
aggcccagca acacagcctc taagttagag cgggatagta acgctgacag agagactatc    900
aacctgaagg aacttgaacc ccaaattgct tcagcaaaac caaatgcaga gtgtactagt    960
cactatccca tagtcccact ggacagcaag atctcgctgc ccatccggaa tggctctgaa    1020
gtgcgggacc cactggtcac ctatgaggga tctctcccac cagcatcccc gctgcaagac    1080
aacctggtta tcgccctgca cagttatgag ccctcccatg atggagactt gggctttgag    1140
aagggtgaac agctccgaat cctggagcag agcggtgagt ggtggaaggc tcagtccctg    1200
```

```
acgactggcc aagaaggctt cattcccttc aacttcgtgg cgaaagcaaa cagcctggag    1260
cctgaacctt ggttcttcaa gaatctgagc cgtaaggacg ccgagcggca gcttttggcg    1320
cccgggaaca cgcatggatc cttcctgatc cgggaaagcg aaagcactgc ggggtccttt    1380
tccctgtcgg tcagagactt cgaccagaac caggagaag tggtgaaaca ttacaagatc    1440
cgtaacctag acaacggtgg cttctacatc tcccctcgta tcacttttcc cggattgcac    1500
gatctagtcc gccattacac caacgcctct gatgggctgt gcacaaagtt gagccgtcct    1560
tgccagaccc agaagcccca gaaaccatgg tgggaggacg aatgggaagt tcccagggaa    1620
acactgaagt tggtggagcg gctgggagct ggccagttcg gggaagtgtg gatggggtac    1680
tacaacggac acacgaaggt ggcggtgaag agtctgaaac aagggagcat gtcccccgac    1740
gccttcctgg ctgaggctaa cctcatgaag cagctgcagc acccgcggct agtccggctt    1800
tatgcagtgg tcacccagga acccatctac atcatcacgg aatacatgga gaacgggagc    1860
ctagtagatt ttctcaagac tccctcgggc atcaagttga atgtcaacaa acttttggac    1920
atggcagccc agattgcaga gggcatggcg ttcatcgaag aacagaatta catccatcgg    1980
gacctgcgcg ccgccaacat cctggtgtct gacacgctga gctgcaagat tgcagacttt    2040
ggcctggcgc gcctcattga ggacaatgag tacacggccc gggaggggc caaatttccc    2100 attaagtgga cagcaccaga agccattaac tatgggacct tcaccatcaa gtcagacgtg    2160
tggtccttcg ggatcttgct tacagagatc gtcacccacg gtcgaatccc ttacccagga    2220
atgaccaacc ctgaagtcat tcagaacctg gagagaggct accgcatggt gagacctgac    2280
aactgtccgg aagagctgta ccacctcatg atgctgtgct ggaaggagcg cccagaggac    2340
cggcccacgt ttgactacct tcggagtgtt ctggatgact tcttcacagc cacagagggc    2400
cagtaccagc cccagcctgg tacctagtga gaattctaca tg                       2442
```

REDIRECTED CELLS WITH MHC CHIMERIC RECEPTORS AND METHODS OF USE IN IMMUNOTHERAPY

CROSS REFERENCE

This application is a 371 application and claims benefit of International Patent Application No. PCT/US16/40177 filed Jun. 29, 2016, which claims benefit of U.S. Provisional Patent Application No. 62/186,865 filed Jun. 30, 2015, the specification(s) of which is/are incorporated herein in their entirety by reference.

GOVERNMENT SUPPORT

This invention was made with government support under Grant No. R01 AI101053 awarded by NIH. The government has certain rights in the invention.

REFERENCE TO SEQUENCE LISTING

Applicant asserts that the information recorded in the form of an Annex C/ST.25 text file submitted under Rule 13ter.1(a), entitled UNIA_1504_PCT_ST25.txt is identical to that forming part of the international application as filed. The content of the sequence listing is incorporated herein by reference in its entirety.

FIELD OF THE INVENTION

The present invention relates to T cells and T cell receptors, more particularly to redirected T cells with engineered receptors, more particularly to redirected cells expressing a chimeric receptor comprising a major histocompatibility complex (MHC) molecule, including redirected cells further comprising a surrogate coreceptor, e.g., as components of a modular chimeric receptor system.

BACKGROUND OF THE INVENTION

T cells normally recognize and respond to peptide antigens embedded within major histocompatibility complex molecules (pMHCs) of antigen presenting cells (APCs) via their TCR-CD3 complex (see FIG. 1A). This eight-subunit TCR-CD3 complex is composed of the TCR, which is the receptor module that binds the pMHC, and the CD3γε, CD3δε, and CD3ζζ signaling modules that connect the TCR to the intracellular signaling machinery (see FIG. 1B). The intracellular domains of the CD3 subunits contain immunoreceptor tyrosine-based activation motifs (ITAMs) that are phosphorylated by the Src kinases, e.g., Lck, Fyn. CD3γ, CD3δ, and CD3ε each contain one ITAM while CD3ζ contains three ITAMs for a total of ten in a single complex. The TCR-CD3 complex does not appear to have any intrinsic Src kinase activity. In fact, coreceptors (e.g., CD4, CD8) appear to sequester Lck away from the TCR-CD3 complex until both a coreceptor and a TCR bind a pMHC. The Lck associated with the coreceptor is then brought into close proximity to the CD3 ITAMs to phosphorylate tyrosines within these motifs and initiate signaling.

Ectopic T cell receptors (TCRs) have been introduced into T cells in an effort to reprogram or alter T cell specificity. However, in some cases, the introduction of ectopic TCRs has been found to lead to cross-pairing events with endogenous TCRs, resulting in novel TCRs with autoimmune specificities. This lead to the use of chimeric antigen receptors (CARs), which are typically designed with (a) an extracellular domain consisting of a single-chain variable fragment (scFv) of a monoclonal antibody directed against a target antigen; (b) a transmembrane domain that does not mediate interactions with other protein subunits; and (c) an intracellular domain consisting of the CD3ζ intracellular signaling domain as well as signaling domains from a variety of other signaling molecules (e.g., CD28, CD27, ICOS, 4-1BB, OX40). Without wishing to limit the present invention to any theory or mechanism, it is believed that CARs do not sufficiently take advantage of the modularity of the existing signaling apparatus, which is optimized to direct T cell activation and effector functions. CARs are likely to be delivering incomplete signals that could have unintended consequences or side effects.

The present invention features novel chimeric receptors (e.g., "MHCRs") comprising a portion of a MHC molecule (e.g., class I, class II, non-classical MHC) and a portion of the TCR. In some embodiments, the MHCR comprises a portion of an antigen peptide. The present invention also features cells, such as T cells, expressing said MHCRs (cells expressing a MHCR are herein referred to as "redirected cells"). The MHCRs are adapted to recognize and bind to appropriate (specific) TCRs. Redirected cells (e.g., redirected T cells) expressing a MHCR would mimic antigen presenting cells (APCs), the cells that normally express MHC molecules. In some cases, binding of a TCR of a target T cell to the MHCR of the redirected cell may then result in destruction of the target T cell; thus, in this case, the redirected cells may function as "anti-T cell" T cells. The present invention is not limited to redirected cells functioning to destroy a target. For example, in some embodiments, the redirected cell is adapted to help reprogram a target cell, e.g., the redirected cell may deliver instructions to the target cell.

The present invention also features engineered cells expressing both an MHCR and an SCR. It was surprisingly discovered that engineered cells co-expressing an MHCR and an SCR had enhanced effects (e.g., increased IL-2 expression, see FIG. 5) as compared to engineered cells expressing a MHCR without co-expression of an SCR. Without wishing to limit the present invention to any theory or mechanism, it is believed that the use of an SCR in combination with a MHCR enhances signaling and/or other downstream effects. Without wishing to limit the present invention to any theory or mechanism, it is believed that the combination of the MHCR and SCR may provide a synergistic effect, e.g., effects of the combination of the MHCR and SCR may provide effects greater than those of the MHCR and SCR individually.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features novel chimeric receptors for engineering redirected cells. For example, the present invention features an engineered cell co-expressing on its surface a chimeric receptor (MHCR) comprising a major histocompatibility complex (MHC) portion (derived from a MHC protein) directly or indirectly fused to a T cell receptor (TCR) portion (derived from a TCR protein); and a surrogate co-receptor (SCR) comprising a cell surface receptor ligand portion directly or indirectly fused to a signaling molecule portion. In some embodiments, the MHCR is adapted to bind to a TCR of a target cell and the SCR is adapted to bind to a cell surface receptor of the target cell. In some embodiments, binding of the MHCR to the TCR of the target cell and binding of the SCR to the cell surface receptor of the target cell (i) initiates a signaling cascade effective for eliminating the target cell or (ii) instructs the target cell to differentiate to a specific effector function. In some embodiments, the cell (e.g., genetically engineered cell) is a T cell (e.g., CD4+, CD8+); however, the present invention is not limited to T cells.

In some embodiments, the TCR portion comprises a transmembrane domain of the TCR protein and the MHC portion comprises an extracellular domain of the MHC protein. In some embodiments, the TCR portion comprises at least a portion of a transmembrane domain of the TCR protein and the MHC portion comprises at least a portion of an extracellular domain of the MHC protein. In some embodiments, the TCR portion comprises at least a portion of a transmembrane domain and at least a portion of a cytoplasmic domain of a TCR protein, and the MHC portion comprises at least a portion of an extracellular domain of the MHC protein.

In some embodiments, the MHC portion of the MHCR is N-terminal to the TCR portion of the MHCR. In some embodiments, the MHC portion is directly fused to the TCR portion. In some embodiments, the MHC portion is indirectly fused to the TCR portion via a linker. In some embodiments, the MHCR further comprises a peptide antigen integrated into the MHC portion, or directly or indirectly fused to the MHC portion. In some embodiments, the peptide antigen is linked to the MHC portion via a linker. In some embodiments, the linker comprises a glycine-rich peptide. In some embodiments, the SCR further comprises a transmembrane domain positioned in between the cell surface receptor ligand portion and the signaling molecule portion. In some embodiments, the MHC protein, the TCR protein, or both the MHC protein and the TCR protein are mammalian proteins (e.g., human, mouse, cat, dog, etc. In some embodiments, the signaling molecule portion has kinase or phosphatase activity. In some embodiments, the signaling molecule portion comprises a Src kinase.

In some embodiments, the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment thereof, or a combination thereof. In some embodiments, the MHC molecule comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a peptide that is at least 90% identical to HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, or H2-EK beta, a fragment thereof, or a combination thereof. In some embodiments, the TCR molecule comprises TRAC, TRBC1, TRBC2, TRDC, TRGC1, TRGC2, TCRA, TCB1, TCB2, TCC1, TCC2, TCC3, TCC4, a fragment thereof, or a combination thereof. In some embodiments, the TCR molecule comprises TRAC, TRBC1, TRBC2, TRDC, TRGC1, TRGC2, TCRA, TCB1, TCB2, TCC1, TCC2, TCC3, TCC4, a peptide that is at least 90% identical to TRAC, TRBC1, TRBC2, TRDC, TRGC1, TRGC2, TCRA, TCB1, TCB2, TCC1, TCC2, TCC3, or TCC4, a fragment thereof, or a combination thereof. In some embodiments, the cell surface receptor ligand portion of the SCR comprises a CD28 ligand, a CTLA-4 ligand, an ICOS ligand, an OX4O ligand, a PD-1 ligand, or a CD2 ligand. In some embodiments, the CD28 ligand comprises CD80, CD86, or both CD80 and CD86. In some embodiments, the MHCR is adapted to complex with a CD3 subunit. In some embodiments, the engineered cell further co-expresses a second SCR.

The present invention also features a chimeric receptor (MHCR) as described above. For example, the MHCR may comprise a major histocompatibility complex (MHC) portion derived from a MHC protein directly or indirectly fused to a T cell receptor (TCR) portion derived from a TCR protein, wherein the MHCR is adapted to bind to a TCR of a target cell.

The present invention also features a method of eliminating a target cell or reprogramming a target cell (the target cell comprising a TCR). In some embodiments, the method comprises introducing a genetically engineered cell that expresses on its surface a chimeric receptor (MHCR) according to the present invention to the target cell, wherein the MHCR is specific for the TCR of the target cell, wherein upon binding of the MHCR to the TCR the genetically engineered cell (a) initiates a signaling cascade that eliminates the target cell, or (b) instructs the target cell to differentiate to a specific effector function. In some embodiments, the method is for immunotherapy. In some embodiments, the target cell is an autoreactive T cell.

The present invention also features vectors encoding MHCRs of the present invention. The present invention also features vectors encoding SCRs of the present invention.

Then present invention also features an engineered cell co-expressing on its surface a chimeric receptor (MHCR) comprising a major histocompatibility complex (MHC) portion derived from an extracellular domain of a mammalian MHC protein directly or indirectly linked to a transmembrane domain of a T cell receptor (TCR) portion derived from a mammalian TCR protein, wherein the MHC portion is N-terminal to the TCR portion; and a surrogate coreceptor (SCR) comprising a cell surface receptor ligand portion indirectly linked to a signaling molecule portion by a transmembrane domain, wherein the signaling molecule portion has kinase or phosphatase activity. The MHCR may be adapted to bind to a TCR of a target cell and the SCR may be adapted to bind to a cell surface receptor of the target cell.

The present invention also features an engineered T-cell co-expressing on its surface: a chimeric receptor (MHCR) comprising a major histocompatibility complex (MHC) portion derived from an extracellular domain of a mammalian MHC protein directly or indirectly linked to a transmembrane domain of a T cell receptor (TCR) portion derived from a mammalian TCR protein, the MHC portion being N-terminal to the TCR portion, the MHC portion being selected from HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, and H2-EK beta, the TCR portion being selected from TRAC, TRBC1, TRBC2, TRDC, TRGC1, TRGC2, TCRA, TCB1, TCB2, TCC1, TCC2, TCC3, TCC4; and a surrogate coreceptor (SCR) comprising a cell surface receptor ligand portion indirectly linked to a signaling molecule portion by a transmembrane domain, the signaling molecule portion having kinase or phosphatase activity. The MHCR may be adapted to bind to a TCR of a target cell and the SCR may be adapted to bind to a cell surface receptor of the target cell.

In some embodiments, the MHC molecule comprises at least a portion of an extracellular domain of a MHC protein.

In some embodiments, the TCR molecule comprises at least a portion of a cytoplasmic domain of a TCR protein, at least a portion of a transmembrane domain of a TCR protein, at least a portion of an extracellular domain of a TCR protein, or a combination thereof. In some embodiments, the chimeric receptor is adapted to bind to a TCR. In some embodiments, the chimeric receptor is adapted to complex with at least one CD3 subunit.

The present invention also features a surrogate co-receptor (SCR) comprising a cell surface receptor ligand portion directly or indirectly fused to a signaling molecule portion via a transmembrane domain, wherein the SCR is adapted to bind to a cell surface receptor of a target cell. In some embodiments, the cell surface receptor ligand portion is indirectly fused to the signaling molecule portion via a linker.

The present invention also features genetically engineered cells (e.g., redirected cells) that express on their surfaces a chimeric receptor according to the present invention. In some embodiments, the cell is a T cell (e.g., CD8+ T cell, CD4+ T cell, etc.). In some embodiments, the cell co-expresses one or more SCRs according to the present invention. In some embodiments, the chimeric receptor is complexed with at least one CD3 subunit.

The present invention also features method of eliminating a target cell or reprogramming a target cell (said target cell comprising a TCR). In some embodiments, the method comprises introducing a genetically engineered cell that expresses on its surface a chimeric receptor to the target cell, wherein the chimeric receptor is specific for the TCR of the target cell. In some embodiments, binding of the chimeric receptor on the genetically engineered cell to the TCR of the target cell initiates a signaling cascade that eliminates the target cell. In some embodiments, binding of the chimeric receptor of the genetically engineered cell to the TCR of the target cell instructs the target cell to differentiate to a specific effector function (e.g. Th1, Th2, Th17, Tfh, Treg or cytotoxic T cell). In some embodiments, the chimeric receptor (e.g., MHCR) is expressed on a Treg and binding of the chimeric receptor to the TCR of a target cell inhibits the target cell's function (e.g., redirect the Treg function against an autoimmune cell). In some embodiments, the genetically engineered cell co-expresses a SCR. In some embodiments, the SCR comprises a cell surface receptor ligand specific for a cell surface receptor on the target cell. In some embodiments, binding of the chimeric receptor to the TCR and binding of the cell surface receptor ligand of the SCR to the cell surface receptor of the target cell initiates a signaling cascade that eliminates the target cell, or instructs the target cell to differentiate to a specific effector function.

In some embodiments, the method is for immunotherapy. In some embodiments, the genetically engineered cell is surgically introduced to a host (e.g., a mammal). In some embodiments, the target cell is an autoreactive T cell.

The present invention also features nucleotide sequences encoding the chimeric receptors of the present invention. The present invention also features vectors encoding the chimeric receptors of the present invention. The present invention also features nucleotide sequences encoding the SCRs of the present invention. The present invention also features vectors encoding the SCRs of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 6 shows TCR-specific killing of CD4 T cells by redirected CTLs. Purified CD8 T cells from B10.A mice were activated in vitro and transduced with a MCC:I-$E^k$ pMHCR (agonist) or an HB:I-$E^k$ pMHCR (null) as well as

DETAILED DESCRIPTION OF THE INVENTION

Chimeric MHC Receptors (MHCRs)

Figure 1A:
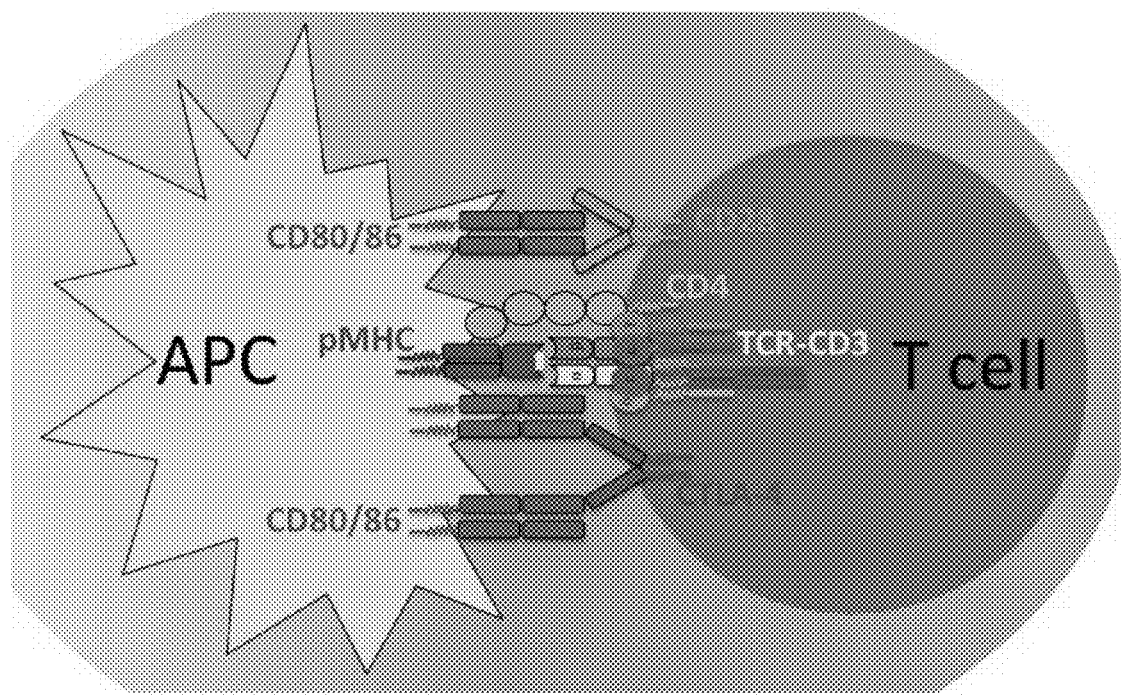
FIG. 1A shows molecules involved in T cell activation. Engagement of the TCR with pMHC (MHC with a peptide antigen) initiates T cell activation.
Figure 1B:
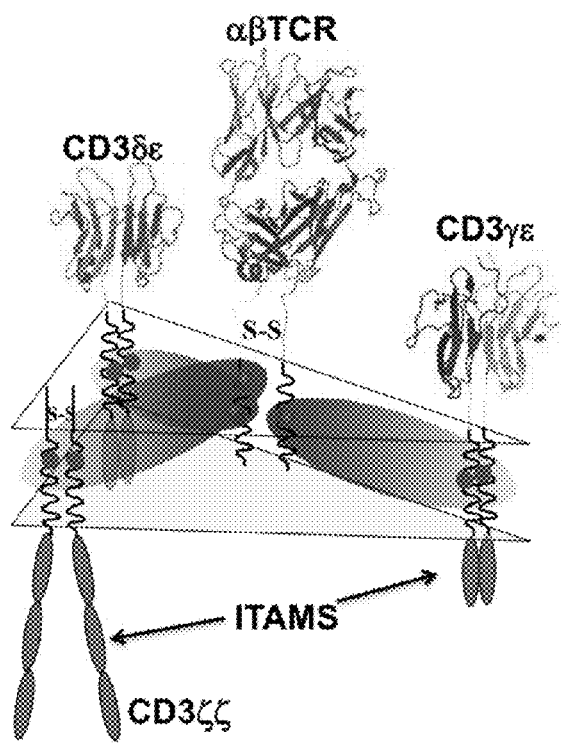
FIG. 1B shows the molecular components of the ☐lpha-beta-TCR-CD3 complex. The TCR transfers pMHC-specific information to the CD3 subunits and inside the T cell. Triangles represent the inner and outer leafs of the cell membrane. Red and blue dots and ovals represent the transmembrane charge interactions that drive subunit assembly of the complexes (from Kuhns et al., 2006, Immunity 24:133-139).
Figure 2A:
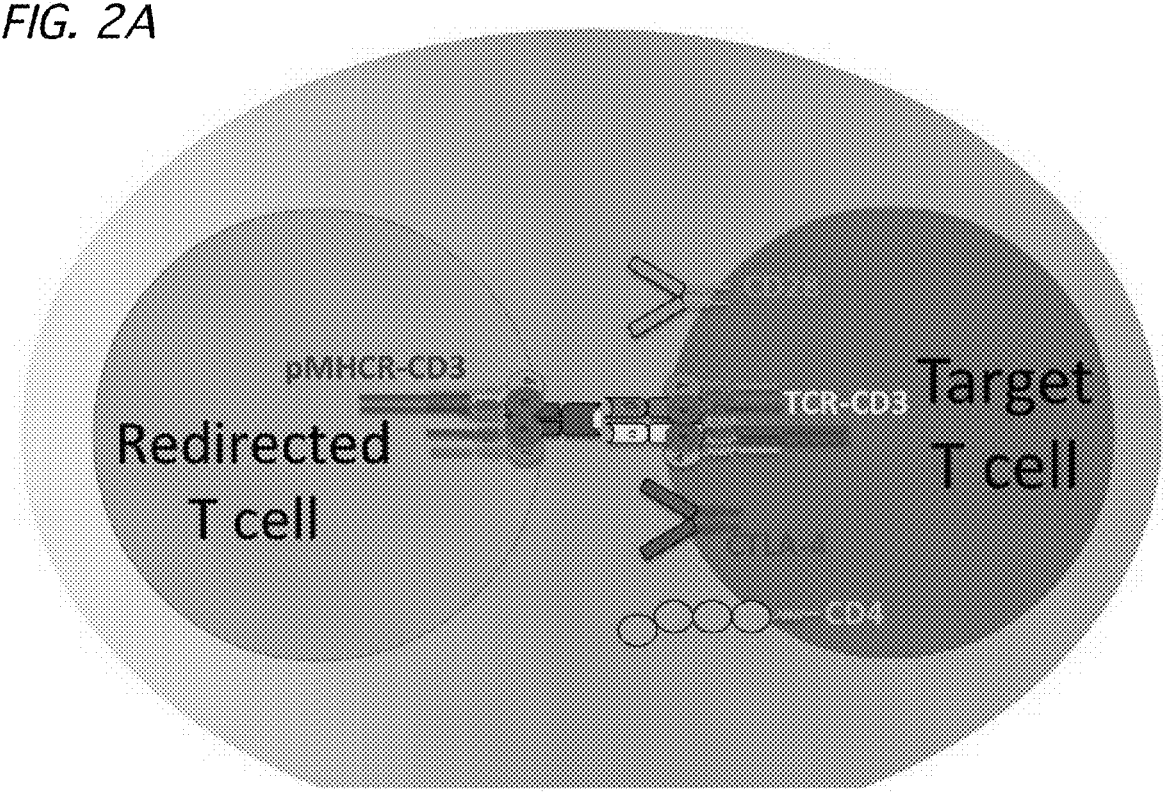
FIG. 2A shows a redirected T cell expressing a MHCR (pMHCR with peptide antigen) of the present invention. The MHCR in complex with CD3 subunits is bound to a target T cell's TCR.
Figure 2B:
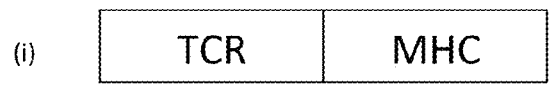
FIG. 2B shows non-limiting examples of MHCR configurations (and the schematics are not limiting with respect to N-terminal and C-terminal orientation). TCR refers to the T cell receptor portion; MHC refers to the major histocompatibility portion, antigen refers to the antigen portion, and L refers to a linker. The present invention is not limited to these configurations. For example, in some embodiments the antigen portion is integrated into the MHC portion. In some embodiments, the MHC portion is N-terminal to the TCR portion (see orientation of sequences below).
Figure 2B:
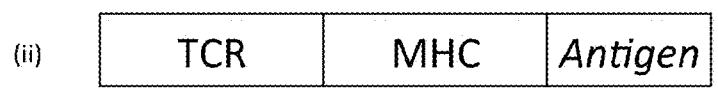
Figure 2B:
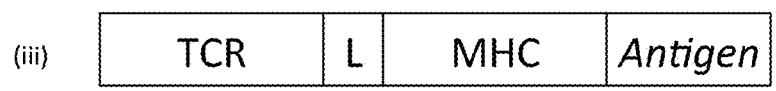
Figure 2B:
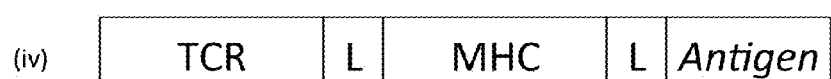
Figure 3A:
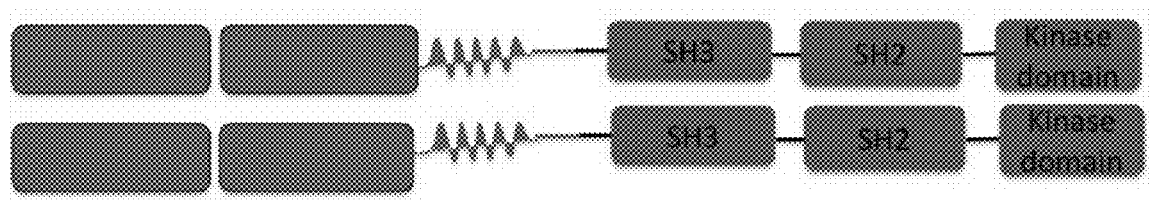
FIG. 3A is a schematic view of a chimeric surrogate coreceptor (SCR), e.g., one comprising CD80/CD86-Lck.
Figure 3B:
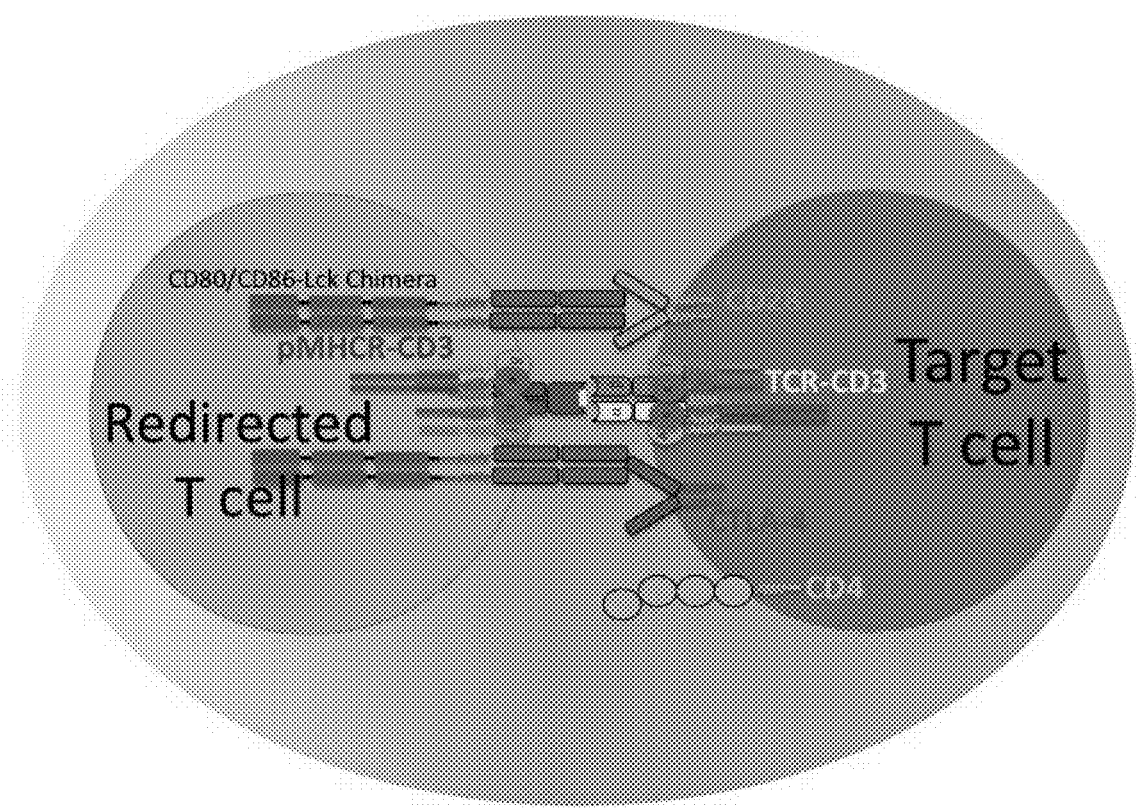
FIG. 3B shows a redirected T cell expressing a MHCR (pMHCR) and two surrogate coreceptors (SCRs). The MHCR, bound to a target T cell's TCR, is complexed with CD3. The SCRs are bound to the target T cell's coreceptors (CD28, CTLA-4). Binding of the SCRs to coreceptors on the target T cell may help initiate CD3 signaling similar to that seen in normal T cell activation.

The present invention features chimeric receptors (e.g., "MHCRs") comprising at least a MHC portion (e.g., class I, class II, non-classical, a combination thereof, etc.) and a TCR portion (e.g., αβ, γδ TCR, etc.) (see FIG. 2B(i)). For example, the MHCR may comprise a MHC portion and a TCR portion, a MHC and a TCR portion optionally separated by a linker (see FIG. 2B (iii) and (iv)). A linker may be any appropriate linker such as but not limited to a peptide linker. In some embodiments, the MHCR further comprises a peptide antigen (see FIG. 2B (ii)); a MHCR comprising a peptide antigen may herein be referred to as a "pMHCR". Note that MHC portions and/or TCR portions may be from any appropriate species including but not limited to human, monkey, mouse, rat, rabbit, or the like, e.g., any other appropriate mammalian species. The components and configurations of the MHRCs of the present invention are not limited to those shown in FIG. 2B. For example, the MHCR may comprise a TCR portion and a MHC portion; a TCR portion and a MHC portion separated by a linker; a TCR portion and a MHC portion and an antigen portion; a TCR portion and a MHC portion and an antigen portion, wherein the TCR portion and MHC portion are separated by a linker; a TCR portion and a MHC portion and an antigen portion, wherein the MHC portion and antigen portion are separated by a linker; a TCR portion and a MHC portion and an antigen portion, wherein the TCR and MHC portion are separated by a linker and the MHC portion and the antigen portion are separate by a linker; etc.

The MHC portion may comprise one or more MHC proteins (e.g., HLA-A, HLA-B, HLA-C, HLA-DPA1, HLA-DPB1, HLA-DQA1, HLA-DQB1, HLA-DRA, HLA-DRB1), one or more fragments thereof, or combinations thereof. For reference, non-limiting MHC sequences (human, mouse) are listed below in Table 1.1 and Table 1.2. Note that MHC genes are highly polymorphic, and thus the present invention is not limited to the sequences in Table 1.1 And Table 1.2. The present invention includes MHC polymorphisms and any other appropriate variant of MHC proteins.

TABLE 1.1

Examples of Human MHC Protein Sequences

| SEQ ID NO. | Description | Amino Acid Sequence |
|---|---|---|
| 1 | Uniprot P01891 HLA-A gene (MHC I) | MAVMAPRTLV LLLSGALALT QTWAGSHSMR YFYTSVSRPG RGEPRFIAVG YVDDTQFVRF DSDAASQRME PRAPWIEQEG PEYWDRNTRN VKAQSQTDRV DLGTLRGYYN QSEAGSHTIQ MMYGCDVGSD GRFLRGYRQD AYDGKDYIAL KEDLRSWTAA DMAAQTTKHK WEAAHVAEQW RAYLEGTCVE WLRRYLENGK ETLQRTDAPK THMTHHAVSD HEATLRCWAL SFYPAEITLT WQRDGEDQTQ DTELVETRPA GDGTFQKWVA VVVPSGQEQR YTCHVQHEGL PKPLTLRWEP SSQPTIPIVG IIAGLVLFGA VITGAVVAAV MWRRKSSDRK GGSYSQAASS DSAQGSDVSL TACKV |
| 2 | Uniprot P18464 HLA-B gene (MHC I) | MRVTAPRTVL LLLWGAVALT ETWAGSHSMR YFYTAMSRPG RGEPRFIAVG YVDDTQFVRF DSDAASPRTE PRAPWIEQEG PEYWDRNTQI FKTNTQTYRE NLRIALRYYN QSEAGSHTWQ TMYGCDVGPD GRLLRGHNQY AYDGKDYIAL NEDLSSWTAA DTAAQITQRK WEAAREAEQL RAYLEGLCVE WLRRHLENGK ETLQRADPPK THVTHHPVSD HEATLRCWAL GFYPAEITLT WQRDGEDQTQ DTELVETRPA GDRTFQKWAA VVVPSGEEQR YTCHVQHEGL PKPLTLRWEP SSQSTIPIVG IVAGLAVLAV VVIGAVVATV MCRRKSSGGK GGSYSQAASS DSAQGSDVSL TA |
| 3 | Uniprot Q29963 HLA-C gene (MHC I) | MRVMAPRTLI LLLSGALALT ETWACSHSMR YFDTAVSRPG RGEPRFISVG YVDDTQFVRF DSDAASPRGE PRAPWVEQEG PEYWDRETQK YKRQAQADRV NLRKLRGYYN QSEDGSHTLQ WMYGCDLGPD GRLLRGYDQS AYDGKDYIAL NEDLRSWTAA DTAAQITQRK WEAAREAEQW RAYLEGTCVE WLRRYLENGK ETLQRAEHPK THVTHHPVSD HEATLRCWAL GFYPAEITLT WQRDGEDQTQ DTELVETRPA GDGTFQKWAA VVVPSGEEQR YTCHVQHEGL PEPLTLRWEP SSQPTIPIVG IVAGLAVLAV LAVLGAVMAV VMCRRKSSGG KGGSCSQAAS SNSAQGSDES LIACKA |

TABLE 1.1-continued

Examples of Human MHC Protein Sequences

| SEQ ID NO. | Description | Amino Acid Sequence |
|---|---|---|
| 4 | Uniprot P20036 HLA DPA1 (MHC II) | MRPEDRMFHI RAVILRALSL AFLLSLRGAG AIKADHVSTY AAFVQTHRPT GEFMFEFDED EMFYVDLDKK ETVWHLEEFG QAFSFEAQGG LANIAILNNN LNTLIQRSNH TQATNDPPEV TVFPKEPVEL GQPNTLICHI DKFFPPVLNV TWLCNGELVT EGVAESLFLP RTDYSFHKFH YLTFVPSAED FYDCRVEHWG LDQPLLKHWE AQEPIQMPET TETVLCALGL VLGLVGIIVG TVLIIKSLRS GHDPRAQGTL |
| 5 | Uniprot P04440 HLA DPB1 (MHC II) | MMVLQVSAAP RTVALTALLM VLLTSVVQGR ATPENYLFQG RQECYAFNGT QRFLERYIYN REEFARFDSD VGEFRAVTEL GRPAAEYWNS QKDILEEKRA VPDRMCRHNY ELGGPMTLQR RVQPRVNVSP SKKGPLQHHN LLVCHVTDFY PGSIQVRWFL NGQEETAGVV STNLIRNGDW TFQILVMLEM TPQQGDVYTC QVEHTSLDSP VTVEWKAQSD SARSKTLTGA GGFVLGLIIC GVGIFMHRRS KKVQRGSA |
| 6 | Uniprot P01909 HLA DQA1 (MHC II) | MILNKALMLG ALALTTVMSP CGGEDIVADH VASYGVNLYQ SYGPSGQYTH EFDGDEQFYV DLGRKETVWC LPVLRQFRFD PQFALTNIAV LKHNLNSLIK RSNSTAATNE VPEVTVFSKS PVTLGQPNIL ICLVDNIFPP VVNITWLSNG HSVTEGVSET SFLSKSDHSF FKISYLTLLP SAEESYDCKV EHWGLDKPLL KHWEPEIPAP MSELTETVVC ALGLSVGLVG IVVGTVFIIR GLRSVGASRH QGPL |
| 7 | Uniprot P01920 HLA DQB1 (MHC II) | MSWKKALRIP GGLRAATVTL MLAMLSTPVA EGRDSPEDFV YQFKAMCYFT NGTERVRYVT RYIYNREEYA RFDSDVEVYR AVTPLGPPDA EYWNSQKEVL ERTRAELDTV CRHNYQLELR TTLQRRVEPT VTISPSRTEA LNHHNLLVCS VTDFYPAQIK VRWFRNDQEE TTGVVSTPLI RNGDWTFQIL VMLEMTPQHG DVYTCHVEHP SLQNPITVEW RAQSESAQSK MLSGIGGFVL GLIFLGLGLI IHHRSQKGLL H |
| 8 | Uniprot P01903 HLA DRA gene (MHC II) | MAISGVPVLG FFIIAVLMSA QESWAIKEEH VIIQAEFYLN PDQSGEFMFD FDGDEIFHVD MAKKETVWRL EEFGRFASFE AQGALANIAV DKANLEIMTK RSNYTPITNV PPEVTVLTNS PVELREPNVL ICFIDKFTPP VVNVTWLRNG KPVTTGVSET VFLPREDHLF RKFHYLPFLP STEDVYDCRV EHWGLDEPLL KHWEFDAPSP LPETTENVVC ALGLTVGLVG IIIGTIFIIK GVRKSNAAER RGPL |
| 9 | Uniprot Q30167 HLA DRB1 gene (MHC II) | MVCLRLPGGS CMAVLTVTLM VLSSPLALAG DTRPRFLEEV KFECHFFNGT ERVRLLERRV HNQEEYARYD SDVGEYRAVT ELGRPDAEYW NSQKDLLERR RAAVDTYCRH NYGVGESFTV QRRVQPKVIV YPSKTQPLQH HNLLVCSVNG FYPGSIEVRW FRNGQEEKTG VVSTGLIQNG DWTFQTLVML ETVPQSGEVY TCQVEHPSVM SPLTVEWRAR SESAQSKMLS GVGGFVLGLL FLGAGLFIYF RNQKGHSGLP PTGFLS |

TABLE 1.2

Examples of Mouse MHC Protein Sequences

| SEQ ID NO. | Description | Amino Acid Sequence |
|---|---|---|
| 10 | Uniprot Q9TQ72 MHC II antigen IE alpha (H2-Aa) | RSRALILGVL ALTTMLSLCG GEDYIEADHV AFYGISVYQS PDIGQYTFE FDGDELFYVD LDKKETVWML PEFGQLTSFD PQGGLQEIAT GKYNLEILIK DSNFTPAANE APQATVFPKS |

TABLE 1.2-continued

Examples of Mouse MHC Protein Sequences

| SEQ ID NO. | Description | Amino Acid Sequence |
|---|---|---|
|  |  | PVLLGQPNTL ICFVDNIFPP VINITWLRNS KSVTDGVYET SFLVNRDHSF HKLSYLTFIP SDDDIYDCKV EHWGLEEPVL KHWEPEIPAP MSELTETVIC ALGLSVGLVG IVVGTIFIIQ GLRSGGTSRH |
| 11 | Uniprot O19440 MHC I antigen (H2-B1) | MAQRTLFLLL AAALTMIETR AGPHSMRYFE TAVFRPGLGE PRFISVGYVD NTQFVSFDSD AENPRSEPRA PWMEQEGPEY WERETQIAKD NEQSFGWSLR NLIHYYNQSK GGFHTFQRLS GCDMGLDGRL LRGYLQFAYD GRDYITLNED LKTWMAADLV ALITRRKWEQ AGAAELYKFY LEGECVEWLR RYLELGNETL LRTDPPKAHV THHPRPAGDV TLRCWALGFY PADITLTWQL NGEELTQDME LVETRPAGDG TFQKWAAVVV PLGKEQNYTC HVYHEGLPEP LTLRWEPPPS TGSNMVNIAV LVVLGAVIII EAMVAFVLKS SRKIAILPGP AGTKGSSAS |
| 12 | Uniprot Q31191 MHC I H2-K gene (Haplotype d) (H2-K1) | MAPCTLLLLL AAALAPTQTR AARAAARGPV RRSGSHRAPP PGPHSLSDAD NPRFEPRAPW MEQEGPEYWE EQTQRAKSDE QWFRVSLRTA QRYYNQSKGG SHTFQRMFGC DVGSDWRLLR GYQQFAYDGR DYIALNEDLK TWTAADTAAL ITRRKWEQAG DAEYYRAYLE GECVEWLRRY LELGNETLLR TDSPKAHVTY HPRSQVDVTL RCWALGFYPA DITLTWQLNG EDLTQDMELV ETRPAGDGTF QKWAAVVVPL GKEQNYTCHV HHKGLPEPLT LRWKLPPPTV SNTVIIAVLV VLGAAIVTGA VVAFVMKMRR NTGGKGVNYA LAPGSQTSDL SLPDGKVMVH |
| 13 | Uniprot P04230 H2 Class II histocompatibility antigen E-B beta chain | MVWLPRVPCV AAVILLLTVL SPPMALVRDS RPWFLEYCKS ECHFYNGTQR VRLLERYFYN LEENLRFDSD VGEFHAVTEL GRPDAENWNS QPEFLEQKRA EVDTVCRHNY EISDKFLVRR RVEPTVTVYP TKTQPLEHHN LLVCSVSDFY PGNIEVRWFR NGKEEKTGIV STGLVRNGDW TFQTLVMLET VPQSGEVYTC QVEHPSLTDP VTVEWKAQST SAQNKMLSGV GGFVLGLLFL GAGLFIYFRN QKGQSGLQPT GLLS |
| 14 | Uniprot P04224 MHC II E-K alpha chain (underlined portion is portion used in SEQ ID NO: 30) | <u>MATIGALVLR FFFIAVLMSS QKSWAIKEEH TIIQAEFYLL PDKRGEFMFD FDGDEIFHVD IEKSETIWRL EEFAKFASFE AQGALANIAV DKANLDVMKE RSNNTPDANV APEVTVLSRS PVNLGEPNIL ICFIDKFSPP VVNVTWLRNG RPVTEGVSET VFLPRDDHLF RKFHYLTFLP STDDFYDCEV DHWGLEEPLR KHWEFEEKTL LPETKENVVC ALGLFVGLVG IVVGIILIMK GIKKRNVVER</u> RQGAL |
| 15 | GenBank ID: M36939.1 MHC II E-K beta chain (underlined portion is used in SEQ ID NO: 31, 32) | <u>MWLPRVPCVAAVILLLTVLSPPVALVRDSRPW FLEYCKSECHFYNGTQRVRLLVRYFYNLEENL RFDSDVGEFRAVTELGRPDAENWNSQPEFLEQ KRAEVDTVCRHNYEIFDNFLVPRRVEPTVTVY PTKTQPLEHHNLLVCSVSDFYPGNIEVRWFRN GKEEKTGIVSTGLVRNGDWTFQTLVMLETVPQ SGEVYTCQVEHPSLTDPVTVEWKAQSTSAQNK</u> MLSGVGGFVLGLLFLGAGLFIYFRNQKGQSGL QPTGLLS |

Referring to Table 1.1, the HLA-A (MHC I) sequence (SEQ ID NO: 1) includes the signal peptide (amino acids 1-24); amino acids 25-308 are believed to make up the extracellular region, amino acids 309-332 are believed to make up the transmembrane region, and amino acids 333-365 are believed to make up the cytoplasmic region. The HLA-B (MHC I) sequence (SEQ ID NO: 2) includes the signal peptide (amino acids 1-24); amino acids 25-308 are believed to make up the extracellular region, amino acids 309-332 are believed to make up the transmembrane region, and amino acids 333-362 are believed to make up the cytoplasmic region. The HLA-C (MHC I) sequence (SEQ ID NO: 3) includes the signal peptide (amino acids 1-24); amino acids 25-308 are believed to make up the extracellular region, amino acids 309-333 are believed to make up the transmembrane region, and amino acids 334-366 are believed to make up the cytoplasmic region. The HLA DPA1 (MHC II) sequence (SEQ ID NO: 4) includes the signal peptide (amino acids 1-28); amino acids 29-222 are believed to make up the extracellular region, amino acids 223-245 are believed to make up the transmembrane region, and amino acids 246-260 are believed to make up the cytoplasmic region. The HLA DPB1 (MHC II) sequence (SEQ ID NO: 5) includes the signal peptide (amino acids 1-29); amino acids 30-225 are believed to make up the extracellular region, amino acids 226-246 are believed to make up the transmembrane region, and amino acids 247-258 are believed to make up the cytoplasmic region. The HLA DQA1 (MHC II) sequence (SEQ ID NO: 6) includes the signal peptide (amino acids 1-23); amino acids 24-216 are believed to make up the extracellular region, amino acids 217-239 are believed to make up the transmembrane region, and amino acids 240-254 are believed to make up the cytoplasmic region. The HLA DQB1 (MHC II) sequence (SEQ ID NO: 7) includes the signal peptide (amino acids 1-32); amino acids 33-230 are believed to make up the extracellular region, amino acids 231-251 are believed to make up the transmembrane region, and amino acids 252-261 are believed to make up the cytoplasmic region. The HLA DRA (MHC II) sequence (SEQ ID NO: 8) includes the signal peptide (amino acids 1-25); amino acids 26-216 are believed to make up the extracellular region, amino acids 217-239 are believed to make up the transmembrane region, and amino acids 240-254 are believed to make up the cytoplasmic region. The HLA DRB1 (MHC II) sequence (SEQ ID NO: 9) includes the signal peptide (amino acids 1-29); amino acids 30-227 are believed to make up the extracellular region, amino acids 228-250 are believed to make up the transmembrane region, and amino acids 251-266 are believed to make up the cytoplasmic region. The MHC E-K alpha chain (SEQ ID NO: 14) includes the signal peptide (aa 1-25), the extracellular domain (aa 26-216), the transmembrane domain (aa 217-24), and a cytoplasmic portion (aa 243-255).

As previously discussed, the MHCR of the present invention comprises at least a MHC portion and a TCR portion. In some embodiments, a MHC portion comprises one or more MHC proteins (e.g., HLA-A, HLA-B, HLA-C, HLA-DPA1, HLA-DPB1, HLA-DQA1, HLA-DQB1, HLA-DRA, HLA-DRB1, MHC E-K alpha, MHC E-K beta, etc.), fragments thereof, or combinations thereof. For example, in some embodiments, the MHC portion comprises a fragment of any of SEQ ID NO: 1-15.

In some embodiments, the MHC portion comprises a peptide that is at least 80% identical to a MHC protein or a fragment thereof. In some embodiments, the MHC portion comprises a peptide that is at least 85% identical to a MHC protein or a fragment thereof. In some embodiments, the MHC portion comprises a peptide that is at least 90% identical to a MHC protein or a fragment thereof. In some embodiments, the MHC portion comprises a peptide that is at least 95% identical to a MHC protein or a fragment thereof. In some embodiments, the MHC portion comprises a peptide that is at least 99% identical to a MHC protein or a fragment thereof.

In some embodiments, a fragment of a MHC protein is from 10 to 25 aa in length. In some embodiments, a fragment of a MHC protein is from 10 to 50 aa in length. In some embodiments, a fragment of a MHC protein is from 10 to 100 aa in length. In some embodiments, a fragment of a MHC protein is from 10 to 150 aa in length. In some embodiments, a fragment of a MHC protein is from 10 to 200 as in length. In some embodiments, a fragment of a MHC protein is from 10 to 250 as in length. In some embodiments, a fragment of a MHC protein is from 10 to 300 as in length. In some embodiments, a fragment of a MHC protein is from 10 to 350 as in length. In some embodiments, a fragment of a MHC protein is from 25 to 50 as in length. In some embodiments, a fragment of a MHC protein is from 25 to 100 aa in length. In some embodiments, a fragment of a MHC protein is from 25 to 150 as in length. In some embodiments, a fragment of a MHC protein is from 25 to 200 as in length. In some embodiments, a fragment of a MHC protein is from 25 to 250 aa in length. In some embodiments, a fragment of a MHC protein is from 25 to 300 as in length. In some embodiments, a fragment of a MHC protein is from 25 to 350 as in length. In some embodiments, a fragment of a MHC protein is from 50 to 100 as in length. In some embodiments, a fragment of a MHC protein is from 50 to 150 as in length. In some embodiments, a fragment of a MHC protein is from 50 to 200 aa in length. In some embodiments, a fragment of a MHC protein is from 50 to 250 aa in length. In some embodiments, a fragment of a MHC protein is from 50 to 300 as in length. In some embodiments, a fragment of a MHC protein is from 50 to 350 aa in length. In some embodiments, a fragment of a MHC protein is from 100 to 150 as in length. In some embodiments, a fragment of a MHC protein is from 100 to 200 as in length. In some embodiments, a fragment of a MHC protein is from 100 to 250 as in length. In some embodiments, a fragment of a MHC protein is from 100 to 300 as in length. In some embodiments, a fragment of a MHC protein is from 100 to 350 as in length. In some embodiments, a fragment of a MHC protein is from 150 to 200 as in length. In some embodiments, a fragment of a MHC protein is from 150 to 250 as in length. In some embodiments, a fragment of a MHC protein is from 150 to 300 as in length. In some embodiments, a fragment of a MHC protein is from 150 to 350 as in length. In some embodiments, a fragment of a MHC protein is from 200 to 250 aa in length. In some embodiments, a fragment of a MHC protein is from 200 to 300 as in length. In some embodiments, a fragment of a MHC protein is from 200 to 350 as in length. In some embodiments, a fragment of a MHC protein is from 250 to 300 as in length. In some embodiments, a fragment of a MHC protein is from 250 to 350 as in length. In some embodiments, a fragment of a MHC protein is more than 350 as in length.

A TCR portion may comprise one or more TCR proteins (e.g., TCRA, TCRB), one or more fragments thereof, or combinations thereof. For reference, non-limiting TCR sequences (human and mouse) are listed below in Table 2.1 and Table 2.2. The present invention is not limited to the TCR sequences in Table 2.1 and Table 2.2.

TABLE 2.1

Examples of Human TCR Protein Sequences

| SEQ ID NO. | Description | Amino Acid Sequence |
|---|---|---|
| 16 | Uniprot P01848 T cell receptor | PNIQNPDPAV YQLRDSKSSD KSVCLFTDFD SQTNVSQSKD SDVYITDKTV LDMRSMDFKS |

TABLE 2.1-continued

Examples of Human TCR Protein Sequences

| SEQ ID NO. | Description | Amino Acid Sequence |
|---|---|---|
|  | alpha chain constant region (TRAC, TCRA) | NSAVAWSNKS DFACANAFNN SIIPEDTFFP SPESSCDVKL VEKSFETDTN LNFQNLSVIG FRILLLKVAG FNLLMTLRLW SS |
| 17 | Uniprot P01850 T cell receptor beta-1 chain constant region (TRBC1) | EDLNKVFPPE VAVFEPSEAE ISHTQKATLV CLATGFFPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSVSYQQ GVLSATILYE ILLGKATLYA VLVSALVLMA MVKRKDF |
| 18 | Uniprot A0A5B9 T cell receptor beta-2 chain constant region (TRBC2, TCRBC2) | DLKNVFPPEV AVFEPSEAEI SHTQKATLVC LATGFYPDHV ELSWWVNGKE VHSGVSTDPQ PLKEQPALND SRYCLSSRLR VSATFWQNPR NHFRCQVQFY GLSENDEWTQ DRAKPVTQIV SAEAWGRADC GFTSESYQQG VLSATILYEI LLGKATLYAV LVSALVLMAM VKRKDSRG |
| 19 | Uniprot B7Z8K6 T cell receptor delta chain constant region (TRDC) | SQPHTKPSVF VMKNGTNVAC LVKEFYPKDI RINLVSSKKI TEFDPAIVIS PSGKYNAVKL GKYEDSNSVT CSVQHDNKTV HSTDFEVKTD STDHVKPKET ENTKQPSKSC HKPKAIVHTE KVNMMSLTVL GLRMLFAKTV AVNFLLTAKL FFL |
| 20 | Uniprot P0CF51 T cell receptor gamma-1 chain constant region (TRGC1) | DKQLDADVSP KPTIFLPSIA ETKLQKAGTY LCLLEKFFPD VIKIHWQEKK SNTILGSQEG NTMKTNDTYM KFSWLTVPEK SLDKEHRCIV RHENNKNGVD QEIIFPPIKT DVITMDPKDN CSKDANDTLL LQLTNTSAYY MYLLLLLKSV VYFAIITCCL LRRTAFCCNG EKS |
| 21 | Uniprot P03986 T cell receptor gamma-2 chain constant region (TRGC2, TCRGC2) | DKQLDADVSP KPTIFLPSIA ETKLQKAGTY LCLLEKFFPD IIKIHWQEKK SNTILGSQEG NTMKTNDTYM KFSWLTVPEE SLDKEHRCIV RHENNKNGID QEIIFPPIKT DVTTVDPKDS YSKDANDVIT MDPKDNWSKD ANDTLLLQLT NTSAYYMYLL LLKSVVYFA IITCCLLGRT AFCCNGEKS |

TABLE 2.2

Examples of Mouse TCR Protein Sequences

| SEQ ID NO. | Description | Amino Acid Sequence |
|---|---|---|
| 22 | Uniprot P01849 T cell receptor alpha chain constant region (TCRA-mouse) (underlined portion refers to sequence also used in SEQ ID NO: 30) | PYIQNPEPAV YQLKDPRSQD STLCLFTDFD SQINVPKTME SGTFITDKTV LDMKAMDSKS NGAIAWSNQT SFTCQDIFKE TNATYPSSDV PCDATLTEKS FETDMNLNFQ NLSVMGLRIL LLKVAGFNLL MTLRLWSS |
| 23 | Uniprot P01852 T cell receptor beta-1 chain constant region (TCB1-mouse) | EDLRNVTPPK VSLFEPSKAE IANKQKATLV CLARGFFPDH VELSWWVNGK EVHSGVSTDP QAYKESNYSY CLSSRLRVSA TFWHNPRNHF RCQVQFHGLS EEDKWPEGSP KPVTQNISAE AWGRADCGIT SASYQQGVLS ATILYEILLG KATLYAVLVS TLVVMAMVKR KNS |
| 24 | Uniprot P01851 T cell receptor beta-2 chain constant region (TCB2-mouse) (underlined portion refers to sequence used in SEQ ID NO: 31, 32) | EDLRNVTPPK VSLFEPSKAE IANKQKATLV CLARGFFPDH VELSWWVNGK EVHSGVSTDP QAYKESNYSY CLSSRLRVSA TFWHNPRNHF RCQVQFHGLS EEDKWPEGSP KPVTQNISAE AWGRADCGIT SASYQGVLS ATILYEILLG KATLYAVLVS GLVLMAMVKK KNS |

TABLE 2.2-continued

Examples of Mouse TCR Protein Sequences

| SEQ ID NO. | Description | Amino Acid Sequence |
|---|---|---|
| 25 | Uniprot P01853 T cell receptor gamma chain constant region C10.5 (TCC1-mouse) | DKRLDADISP KPTIFLPSVA ETNLHKTGTY LCLLEKFFPD VIRVYWKEKN GNTILDSQEG DTLKTKGTYM KFSWLTVPER AMGKEHSCIV KHENNKGGAD QEIFFPSIKK VATTCWQDKN DVLQFQFTST SAYYTYLLLL LKSVIYLAII SFSLLRRTSV CGNEKKS |
| 26 | Uniprot P03985 T cell receptor gamma chain constant region C7.5 (TCC2-mouse) | DKKLDADISP KPTIFLPSVA ETNLHKTGTY LCVLEKFFPD VIRVYWKEKK GNTILDSQEG DMLKTNDTYM KFSWLTVPER SMGKEHRCIV KHENNKGGAD QEIFFPTIKK VAVSTKPTTC WQDKNDVLQL QFTITSAYYT YLLLLLKSVI YLAIISFSLL RRTSVCCNEK KS |
| 27 | Uniprot P06334 T cell receptor gamma chain constant region DFL12 (TCC3-mouse) | PSDKRLDADI SPKPTIFLPS VAETNLHKTG TYLCILEKFF PDVIRVYWKD KNGNTILDSQ EGDTLKTKGT YMKFSWLTVP ERSMGKEHRC IVKHENNKGG ADQEIFFPSI KKVATTCWQD KNDVLQLQFM STSAYYTYLL LLLKSVIYLA IISFSLLRRT SVCCNEKRS |
| 28 | Uniprot P06335 T cell receptor gamma chain constant region 5/10-13 (TCC4-mouse) | DKRTDSDFSP KPTIFLPSAA ETNLHKAGTY LCLLEKFFPK VIRVYWKEKD GEKILESQEG NTIKTNDRYM KFSWLTVTED SMAKEHSCIV KHENNKRGVD QEILFPPIGK AFTTINVNPR DSVLRHENVN NATDLEDCMK GRKDMLQLQV TTTYAFYTYL ILFFKSMVHL AFVVFCLFRR AAMSCDDQRS |

Referring to the TRAC protein (SEQ ID NO: 16) in Table 2, amino acids 118-137 are believed to make up the transmembrane domain, and amino acids 138-142 are believed to make up the cytoplasmic domain. Referring to the TRBC1 protein (SEQ ID NO: 17) in Table 2, amino acids 151-171 are believed to make up the transmembrane domain. Referring to the TRBC2 protein (SEQ ID NO: 18) in Table 2, amino acids 145-167 are believed to make up the transmembrane domain. Referring to the TRDC protein (SEQ ID NO: 19) in Table 2, amino acids 130-152 are believed to make up the transmembrane domain. Referring to the TRGC1 protein (SEQ ID NO: 20) in Table 2, amino acids 139-161 are believed to make up the transmembrane domain. Referring to the TRGC2 protein (SEQ ID NO: 21) in Table 2, amino acids 157-177 are believed to make up the transmembrane domain, and amino acids 178-189 are believed to make up the cytoplasmic domain.

As previously discussed, the MHCR of the present invention comprises at least a MHC portion and a TCR portion. In some embodiments, a TCR portion comprises one or more TCR proteins (e.g., TRAC, TRBC1, TRBC2, TRDC, TRCG1, TRCG2, TCRA-mouse, TCB1-mouse, TCB2-mouse, TCC1-mouse, TCC2-mouse, TCC3 mouse, TCC4 mouse, etc.), fragments thereof, or combinations thereof. For example, in some embodiments, the TCR portion comprises a fragment of any of SEQ ID NO: 16-28. (In some embodiments, the fragment is from 5 to 10 as in length. In some embodiments, the fragment is from 10 to 20 aa in length, in some embodiments, the fragment is from 10 to 30 as in length. IN some embodiments, the fragment is from 10 to 40 aa in length. In some embodiments, the fragment is from 10 to 50 as in length, etc.

In some embodiments, the TCR portion comprises a peptide that is at least 80% identical to a TCR protein (e.g., any of SEQ ID NO: 16-28), or a fragment thereof. In some embodiments, the TCR portion comprises a peptide that is at least 85% identical to a TCR protein (e.g., any of SEQ ID NO: 16-28), or a fragment thereof. In some embodiments, the TCR portion comprises a peptide that is at least 90% identical to a TCR protein (e.g., any of SEQ ID NO: 16-28), or a fragment thereof. In some embodiments, the TCR portion comprises a peptide that is at least 95% identical to a TCR protein (e.g., any of SEQ ID NO: 16-28), or a fragment thereof. In some embodiments, the TCR portion comprises a peptide that is at least 99% identical to a TCR protein (e.g., any of SEQ ID NO: 16-28), or a fragment thereof.

In some embodiments, a fragment of a TCR protein is from 10 to 25 as in length. In some embodiments, a fragment of a TCR protein is from 10 to 50 aa in length. In some embodiments, a fragment of a TCR protein is from 10 to 100 aa in length. In some embodiments, a fragment of a TCR protein is from 10 to 150 aa in length. In some embodiments, a fragment of a TCR protein is from 25 to 50 as in length. In some embodiments, a fragment of a TCR protein is from 25 to 100 as in length. In some embodiments, a fragment of a TCR protein is from 25 to 150 as in length. In some embodiments, a fragment of a TCR protein is from 50 to 100 as in length. In some embodiments, a fragment of a TCR protein is from 50 to 150 as in length. In some embodiments, a fragment of a TCR protein is from 100 to 150 aa in length. In some embodiments, a fragment of a TCR protein is more than 150 aa in length.

In some embodiments, the MHCR comprises a peptide antigen. Any appropriate peptide antigen may be used. The peptide antigen in the pMHCR complex directs the specificity of the pMHCR molecule, therefore the pMHCR molecule will be specific for T cells with TCRs that are specific for that peptide antigen/pMHCR. A non-limiting example of a peptide antigen that may be used with the MHCR is moth cytochrome c peptide (as 88-103, ANERADLIAYLKQATK (SEQ ID NO: 29)). The peptide antigens used in the Examples (see below) are peptides commonly used as model antigens in mouse models. Any appropriate peptide antigen may be used, and the present invention is not limited to the peptide antigens disclosed herein. For example, in some embodiments, the peptide antigen comprises any immunodominant peptide antigen identified to bind a class I or class II MHC. In some embodiments, the peptide antigen comprises any immunodominant peptide antigen identified to bind a class I or class II MHC and elicit a response. A response may include but is not limited to an autoimmune response, an allergic response, an asthma response, or an inappropriate Treg response. The peptide antigen may be any appropriate length.

In some embodiments, the MHCR comprises at least a portion of a MHC molecule that allows for binding to an appropriate TCR. In some embodiments, the MHCR comprises at least a portion of a MHC molecule that allows for binding to an appropriate TCR and at least a portion of a TCR molecule (e.g., a portion of a TCR molecule that allows for appropriate signaling and/or complexing subunits such as CD3 subunits). In some embodiments, the MHCR comprises a transmembrane domain that is at least partially derived from (i) a MHC molecule, (ii) a TCR molecule, or (iii) both the MHC molecule and TCR molecule. In some embodiments, the MHCR comprises a transmembrane domain, wherein a portion (or all) of the transmembrane domain is not derived from a MHC molecule or a TCR molecule. In some embodiments, the MHCR comprises an extracellular domain that is at least partially derived from (i) a MHC molecule, (ii) a TCR molecule, or (iii) both the MHC molecule and TCR molecule. In some embodiments, the MHCR comprises an extracellular domain, wherein a portion of the extracellular domain is not derived from a MHC molecule or a TCR molecule.

As an example, in some embodiments, the MHCR comprises at least a portion of the extracellular domain of a MHC molecule (e.g., the extracellular domain of HLA-DRA) and at least a portion of the transmembrane domain of a TCR molecule and at least a portion of the cytoplasmic domain of a TCR molecule. As another example, in some embodiments, the MHCR comprises at least a portion of the extracellular domain of a TCR molecule.

The present invention also features redirected cells, such as redirected T cells, expressing MHCRs of the present invention, e.g., as described above. Without wishing to limit the present invention to any theory or mechanism, the MHCRs are generally adapted to recognize and bind to appropriate (specific) TCRs. In some embodiments, the MHCR is expressed in a CD8+ T cell (e.g., a cytotoxic T cell, $T_C$ cells, CTLs). In some embodiments, the MHCR is expressed in a CD4+ T cell (e.g., a T helper cell, $T_H$ cell or a regulatory T cell (Treg cell)). The present invention is not limited to the expression of MHCRs in T cells, nor is the present invention limited to expression of MHCRs in CD8+ or CD4+ T cells, e.g., the MHCRs may be expressed in CD8+/CD4+ thymocytes, γδT cells, NK cells, NK T cells, etc. In some embodiments, the MHCR of the redirected T cell complexes or is adapted to complex with CD3 subunits (e.g., forming a MHCR-CD3 complex).

In some embodiments, the MHCR comprises a MHC portion derived from an extracellular portion of a MHC protein and a TCR portion derived from a transmembrane domain of a TCR protein. In some embodiments, the MHC portion and TCR portion are directly linked. In some embodiments, the MHC portion and TCR portion are separated by a linker. In some embodiments, the linker comprises a glycine-rich linker.

The present invention is not limited to the MHC portions and TCR portions described herein. For example, the MHC portion may comprise any MHC peptide, e.g., an extracellular domain (or a portion thereof) of any MHC peptide. The TCR portion may comprise any TCR peptide, e.g., a transmembrane domain (or portion thereof) of any TCR peptide. Further, the present invention is not limited to antigens, signaling molecules, and cell surface receptor ligands described herein, e.g., the present invention may be applicable to a wide range of MHC molecules, TCR molecules, antigens, signaling molecules cell surface receptor ligands, etc.

Surrogate Coreceptors (SCRs)

The present invention also features chimeric surrogate coreceptors (SCR). e.g., receptors that recruit signaling molecules (e.g., kinases such as but not limited to Src kinases (e.g., Lck), phosphatases, etc.). In some embodiments, the SRCs recruit signaling molecules (e.g., kinases) to the MHCR and/or CD3 subunits. The present invention also features cells expressing a SCR. In some embodiments, redirected cells, e.g., redirected T cells, express both a MHCR and a SCR. In some embodiments, cells express more than one type of SCR. Without wishing to limit the present invention to any theory or mechanism, it is believed that certain SCRs may enhance signaling through the pMHCR-CD3 complex.

In some embodiments, the SCR comprises a cell surface receptor ligand (e.g., T cell surface receptor ligand) fused to a signaling molecule (e.g., kinase (e.g., Lck or other appropriate kinase), phosphatase, etc.). In some embodiments, the cell surface receptor ligand and the kinase are separated by a linker, e.g., a peptide linker or any other appropriate linker. The signaling molecule is not limited to a kinase or a phosphatase.

In some embodiments, the cell surface receptor ligand (e.g., T cell surface receptor ligand) comprises CD80, CD86, fragments thereof, or combinations thereof. The present invention is not limited to CD80 and CD86; any other appropriate cell surface receptor ligand (or a fragment thereof) may be used. For example, in some embodiments, the cell surface receptor ligand comprises a CD28 ligand, a CTLA-4 ligand, an ICOS ligand, an OX4O ligand, a PD-1 ligand (e.g., PD-1L), a CD2 ligand, etc.

As an example, in some embodiments, when a T cell is expressing a pMHCR (a MHCR with a peptide antigen), the pMHCR may complex with CD3 subunits, forming a pMHCR-CD3 complex. If the cell is also expressing a CD80-Lck SCR, then when the pMHCR binds a TCR on a target T cell, the CD80-Lck may also bind to CD28 on the same target T cell. Without wishing to limit the present invention to any theory or mechanism, it is believed that then the CD80-Lck SCR should recruit Lck to the pMHCR-CD3 complex to phosphorylate the pMHCR-CD3 ITAMs for robust signaling.

In some embodiments, the SCR is engineered (e.g., a particular cell surface receptor ligand of the SCR is selected) to target a specific set of target cells. For example, T follicular helper cells express a molecule called PD-1 and these cells provide help to B cells to make autoantibodies in autoimmune diseases such as Lupus. The ligand for PD-1 is PD-1L, so a SCR comprising PD-1L and Lck may be co-expressed with a pMHCR recognized by the TCR of the T follicular helper cell. This may allow for targeting of this specific T follicular helper cell population.

The present invention also features methods of use of said MHCRs, SCRs, and/or said redirected cells, for example for immunotherapy. In some embodiments, the redirected cells may eliminate autoreactive T cells, regulatory T cells (Tregs) that protect tumor cells by suppressing anti-tumor T cell responses, or any other appropriate T cell. For example, in some embodiments, the MHCR is an auto-antigen MHCR, and the MHCR's target is an autoreactive T cell.

EXAMPLES

Example 1: Redirected T Cells Targeting CD4 T Helper Cells

Figure 4:
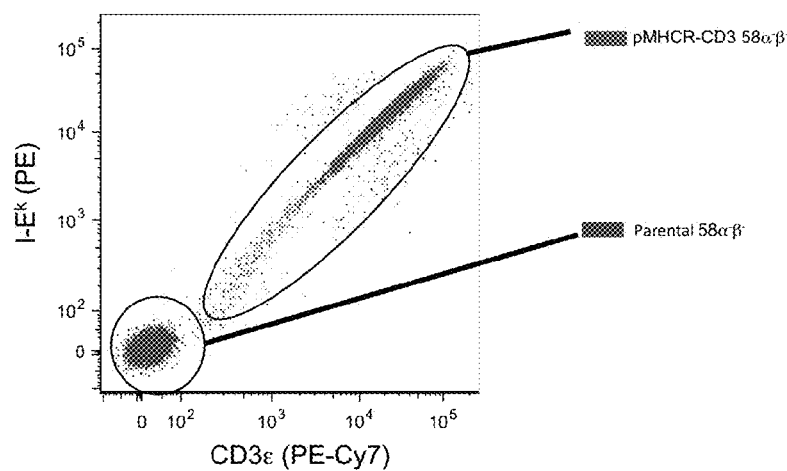
FIG. 4 shows expression of pMHCR-CD3 complexes on T cell hybridomas. $58\alpha^-\beta^-$ cells that lack endogenous TCRs were transduced with a pMHCR composed of MCC:I-$E^k$. The proportional expression (diagonal) of I-$E^k$ and CD3 subunits suggests surface co-dependent expression of the epitopes.

Example 1 describes a non-limiting experimental approach to target CD4 T cells. A prototype pMHCR was engineered with a peptide antigen: the moth cytochrome c peptide (SEQ ID NO: 29) was fused to the mouse class II MHC I-$E_k$ (MCC:I-$E^k$; e.g., see SEQ ID NO: 31). This pMHCR was expressed (e.g., retrovirally expressed) in T cell hybridomas. It was determined that this pMHCR (e.g., pMHCR-CD3 complex) was expressed on the surface of T cell hybridomas (see FIG. 4). IL-2 production was induced after interactions with cognate TCRs (e.g., 5c.c7, 284), yet an irrelevant peptide (control peptide antigen) in the pMHCR-CD3 complex rendered it non-stimulatory (data not shown).

Figure 5:
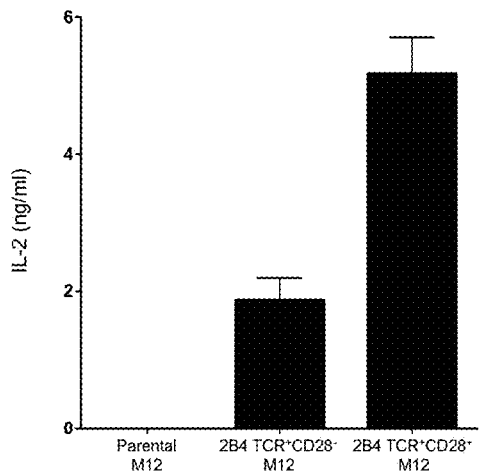
FIG. 5 shows TCR-specific IL-2 production by pMHCR-CD3 expressing T cell hybridomas. $58\alpha^-\beta^-$ cells that lack endogenous TCRs were transduced with a pMHCR composed of MCC:I-$E^k$ as well as a CD80-Lck surrogate coreceptor (SCR). The cells were co-cultured with parental M12 B cells, or M12 cells stably transduced to express the MCC:I-$E^k$-specific 284 TCR alone or with CD28. The increased IL-2 expression in the presence of CD28 indicates that the surrogate coreceptor (SCR) enhances pMHCR-CD3 signaling.

Lck fusions were generated with known ligands for T cell surface receptors. For example, all T cells express CD28. Lck fusions with CD28 ligands (e.g., CD80, CD86) were engineered to generate surrogate coreceptors (SCRs), e.g., CD80-Lck (see SEQ ID NO: 33, SEQ ID NO: 38), e.g., CD86-Lck (see SEQ ID NO: 34, SEQ ID NO: 39). When the pMHCR-CD3 complex was co-expressed with SCR CD80-Lck in hybridomas, these cells produced significantly more IL-2 in response to cells expressing the 2B4 TCR ligand+ CD28 than they did in response to cells expressing only the 284 TCR ligand (see FIG. 5). This suggested that signaling through the pMHCR-CD3 complex could be augmented through the use of a SCR.

Figure 6:
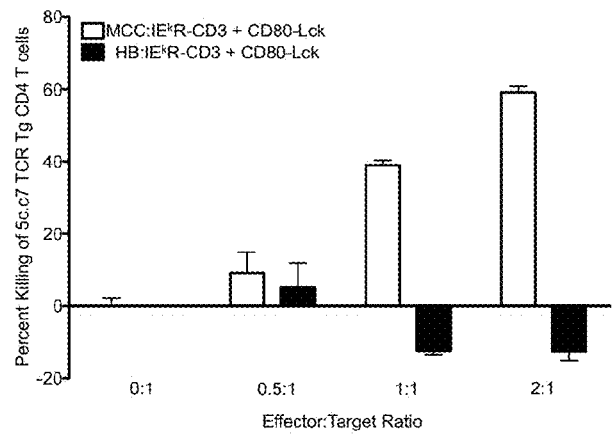

MCC:$IE^k$ pMHCR-CD3 and the SCR CD80-Lck or HB:$IE^k$ pMHCR-CD3 (e.g., see SEQ ID NO: 32) and the SCR CD80-Lck were expressed in in vitro differentiated CD8 cytotoxic T cells (CTLs) and their ability to kill 5c.c7 TCR transgenic CD4 T cells expressing the TCR specific for the MCC:$IE^k$ pMHCR was evaluated. Surface expression of the pMHCRs on the redirected CTLs was observed, suggesting that these chimeric receptor modules compete with the endogenous TCR for assembly with the endogenous CD3 subunits (data not shown). CTLs expressing the MCC:$IE^k$ pMHCR robustly killed the target CD4 T cells while those expressing the null HB:$IE^k$ pMHCR did not (see FIG. 6). This suggests that CD8 T cells can be redirected to target and eliminate antigen-specific CD4 T cells.

Example 2: Redirected T Cells Targeting CD4 T Helper Cells in Allergic Asthma

Example 2 describes a non-limiting experimental approach to target CD4 T helper cells involved in allergic asthma, e.g., to help eliminate naïve Der p 1-specific CD4 T cells from the repertoire prior to House Dust Mite (HDM) sensitization. Without wishing to limit the present invention to any theory or mechanism, it is believed that eliminating allergen-specific CD4 T cells from the repertoire may help prevent the onset of $T_H2$ immunity upon HDM sensitization.

A pMHCR (pMHCR-CD3 complex) will be retrovirally expressed in in vitro activated CTLs. The pMHCR will bear a pMHCR comprising either the immunodominant HDM-derived Der p 1 epitope (aa 17-127) in the context of I-$A^b$ (Derp1:I$A^b$) or the immunodominant West Nile Virus peptide from the envelope protein (aa641-655) in the context of I-$A^b$ (E641:I$A^b$). The E641:I$A^b$ pMHCR cells will serve as a non-specific control population.

The in vitro activated CTLs will also be transduced with a CD80-Lck SCR to enhance signaling. These redirected CTLs will then be transferred intravenously into C57Bl/6 mice to target and eliminate Derp1:I$A^b$- or E641:I$A^b$-specific naïve CD4 T cells from the endogenous repertoire. After a certain length of time, e.g., 1 week, the elimination of antigen-specific CD4 T cells will be evaluated. This will be performed via tetramer enrichment experiments using a Derp1:I$A^b$ tetramer and a E641:I$A^b$ tetramer. The presence of the redirected CD8 T cells will also be assessed by flow cytometry by gating on $CD3^+CD8^+IA^{b+}$ T cells since mouse T cells do not express class II MHC.

After determining if the redirected CTLs eliminate the target population, mice that received redirected CTLs one-week prior will be sensitized with HDM (e.g., intranasally, e.g., with HDM extracts). This will be done even if endogenous CD4 T cells specific for Derp1:I$A^b$ are detected, but only if redirected T cells are still present in the mice. This may help to determine if activation of the CD4 T cells made them more susceptible to targeting by the redirected CTLs.

Example 3: Redirected T Cells Targeting CD4 T Helper Cells in Lungs after Sensitization Example 3 describes a non-limiting experimental approach to target CD4 T helper cells in lungs of HDM-sensitized mice. Without wishing to limit the present invention to any theory or mechanism, it is believed that eliminating allergen-specific CD4 T cells from the lungs of HDM-sensitized mice may help attenuate $T_H2$ immunity.

Der p 1-specific CD4 T cells will be targeted similarly to Example 2, but only after HDM sensitization. In brief, mice will be sensitized with HDM according to the protocol described above. They will then receive redirected Derp1: I$A^b$ or E641:I$A^b$ pMHCR-CD3 CTLs on day 14. Various surrogate co-receptors will be employed to explore the efficacy of the technology and approach. For example, the CD80-Lck fusion SCR will be used, as well as others, e.g., a TIM-4-Lck SCR (since the TIM-1 expressed on CD4 T cells is genetically linked with asthma and this combination for targeting might enhance effectiveness). One week after transfer of redirected CTLs, cytokine and cellular analysis will be performed as described above in Example 2 so as to assess the impact of these cells on the lung cytokine milieu and cellularity. The status of the redirected CTLs will also be evaluated.

Example 4: Attenuation of Der p 1-Specific CD4 T Cell Function In Situ

Example 4 describes a non-limiting experimental approach to redirect Tregs against Der p 1-specific CD4 T cells. Without wishing to limit the present invention to any theory or mechanism, it is believed that this may help attenuate function of said CD4 T cells and help diminish $T_H2$ immunity.

In vitro generated induced Tregs (iTregs) expressing a MHCR will be tested for efficacy in reducing HDM-induced airway hypersensitivity. Induced Tregs (iTregs) will be generated in vitro and transduced with pMHCR and SCRs as described in Examples 2 and 3 above. These cells will then either be transferred prior to HDM sensitization as in Example 2 or after sensitization as in Example 3. Evaluation of the lung cytokine milieu and cellularity will then be performed as described above.

Table 3 shows examples of protein sequences for reagents the above examples. Table 4 shows the nucleotide sequences for the proteins in Table 3. Note that in SEQ ID NO: 30, a portion is derived from SEQ ID NO: 14 and a portion is derived from SEQ ID NO: 22. In SEQ ID NO: 31, a portion is derived from SEQ ID NO: 15, a portion is derived from SEQ ID NO: 23, and a portion is derived from SEQ ID NO: 29 (and other residues may correspond to a glycine-rich linking region). In SEQ ID NO: 32, a portion is derived from SEQ ID NO: 15 and a portion is derived from SEQ ID NO: 23 (and other residues may correspond to a glycine-rich linking region).

TABLE 3

Peptide sequences for reagents in Examples.

| SEQ ID NO. | Description | Amino Acid Sequence |
|---|---|---|
| 30 | I-E$^k$α-TCRα Note: underlined portion is from SEQ ID NO: 14 (MHC portion), bold portion is from SEQ ID NO: 22 (TCR portion) | MATIGALLLRFFFIAVLMSSCIKSWAIKEEHTIIQ AEFYLLPDKRGEFMFDFDGDEIPHVDIEKSETIWR LEEFAKFASFEAQGALANIAVDKANLDVMKERSNN TPDANVAPEVTVLSRSPVNLGEPNILICFIDKFSP PVVNVTWFRNGRPVTEGVSETVFLPRDDHLFRKFH YLTFLPSTDDFYDCEVDHWGLEEPLRKHWEFEEKT LLPETKECDATLTEKSFETDMNLNFQNLSVMGLRI LLLKVAGFNLLMTLRLWSS |
| 31 | MCC: I-E$^k$β-TCRβ (note: italic portion shows peptide antigen sequence, underlined portion is from SEQ ID NO: 15 (MHC portion), and bold portion is from SEQ ID NO: 24 (TCR portion) | MVWLPRVPCVAAVILLLTVLSPPVALVRDSGSA*NE RADLIAYLKQA*TKEFRSGGGGSLVPRGSGGGGSVD RPWFLEYCKSECHFYNGTQRVRLLVRYFYNLEENL RFDSDVGEFRAVTELGRPDAENWNSQPEFLEQKRA EVDTVCRHNYEIFDNFLVPRRVEPTVTVYPTKTQP LEHHNLLVCSVSDFYPGNIEVRWFRNGKEEKTGIV STGLVRNGDWTFQTLVMLETVPQSGEVYTCQVEHP SLTDPVTVEWKAQSTSAQNKCGITSASYHQGVLSA TILYEILLGKATLYAVLVSGLVLMAMVKKKNSAAA |
| 32 | HB: I-E$^k$β-TCRβ Note: italic portion shows peptide antigen sequence, underlined portion is from SEQ ID NO: 15 (MHC portion), and bold portion is from SEQ ID NO: 24 (TCR portion) | MVWLPRVPCVAAVILLLTVLSPPVALVRDSGSGKK *VITAFNEGL*KEFRSGGGGSLVPRGSGGGGSVDRPW FLEYCKSECHFYNGTQRVRLINRYFYNLEENLRFD SDVGEFRAVTELGRPDAENWNSCPEFLEQKRAEVD TVCRHNYEIFDNFLVPRRVEPTVTVYPTKTQPLEH HNLLVCSVSDFYPGNIEVRWFRNGKEEKTGIVSTG LVRNGDWTFQTLVMLETVPQSGEVYTCQVEHPSLT DPVTVEWKAQSTSAQNKCGITSASYHQGVLSATIL YEILLGKATLYAVLVSGLVLMAMVKKKNSAAA |
| 33 | CD80-Lck (mCD80-mLck fusion) | MACNCQLMQDTPLLKFPCPRLILLFVLLIRLSQVS SDVDEQLSKSVKDKVLLPCRYNSPHEDESEDRIYW QKHDKVVLSVIAGKLKVWPEYKNRTLYDNTTYSLI ILGLVLSDRGTYSCVVQKKERGTYEVKHLALVKLS IKADFSTPNITESGNPSADTKRITCFASGGFPKPR FSWLENGRELPGINTTISQDPESELYTISSQLDFN TTRNHTIKCLIKYGDAHVSEDFTWEKPPEDPPDSK NTLVLFGAGFGAVITVVVIVVIIKCFCKHRSCFRR NEASRETNNSLTFGPEEALAEQTVFLTISHYPIVP LDSKISLPIRNGSEVRDPLVTYEGSLPPASPLQDN LVIALHSYEPSHDGDLGFEKGEQLRILEQSGEWWK AQSLTTGQEGFIPPNFVAKANSLEPEPWFFKNLSR KDAERQLLAPGNTHGSFLIRESESTAGSFSLSVRD FDQNQGEVVKHYKIRNLDNGGFYISPRITFPGLHD LVRHYTNASDGLCTKLSRPCQTQKPQKPWWEDEWE VPRETLKLVERLGAGQFGEVWMGYYNGHTKVAVKS LKQGSMSPDAFLAEANLMKQLQHPRLVRLYAVVTQ EPIYIITEYMENGSLVDFLKTPSGIKLNVNKLLDM AAQIAEGMAFIEEQNYIHRDLRAANILVSDTLSCK IADFGLARLIEDNEYTAREGAKFPIKWTAPEAINY GTFTIKSDVWSFGILLTEIVTHGRIPYPGMTNPEV IQNLERGYRMVRPDNCPEELYHLMMLCWKERPEDR PTFDYLRSVLDDFFTATEGQYQPQPGT |
| 34 | CD86-Lck (mCD86-mLck fusion) | MDPRCTMGLAILIFVTVLLISDAVSVETQAYFNGT AYLPCPFTKAQNISLSELVVFWQDQQKLVLYEHYL GTEKLDSVNAKYLGRTSFDRNNWTLRLHNVQIKDM GSYDCFIQKKPPTGSIILQQTLTELSVIANFSEPE IKLAQNVTGNSGINLTCTSKQGHPKPKKMYFLITN STNEYGDNMQISQDNVTELFSISNSLSLSFPDGVW HMTVVCVLETESMKISSKPLNFTQEFPSPQTYWKE ITASVTVALLLVMLLIIVCHKKPNQPSRPSNTASK LERDSNADRETINLKELEPQIASAKPNAECTSHYP IVPLDSKISLPIRNGSEVRDPLVTYEGSLPPASPL |

TABLE 3-continued

Peptide sequences for reagents in Examples.

| SEQ ID NO. | Description | Amino Acid Sequence |
|---|---|---|
| | | QDNLVIALHSYEPSHDGDLGFEKGEQLRILEQSGE WWKAQSLTTGQEGFIPFNFVAKANSLEPEPWFFKN LSRKDAERQLLAPGNTHGSFLIRESESTAGSFSLS VRDFDQNQGEVVKHYKIRNLDNGGFYISPRITFPG LHDLVRHYTNASDGLCTKLSRPCQTQKPQKPWWED EWEVPRETLKLVERLGAGQFGEVWMGYYNGHTKVA VKSLKQGSMSPDAFLAEANLMKQLQHPRLVRLYAV VTQEPIYIITEYMENGSLVDFLKTPSGIKLNVNKL LDMAAQIAEGMAFIEEQNYIHRDLRAANILVSDTL SCKIADFGLARLIEDNEYTAREGAKFPIKWTAPEA INYGTFTIKSDVWSFGILLTEIVTHGRIPYPGMTN PEVIQNLERGYRMVRPDNCPEELYHLMMLCWKERP EDRPTFDYLRSVLDDFFTATEGQYQPQPGT |

TABLE 4

Examples of DNA sequences for encoding the proteins in Table 3.

| SEQ ID NO. | Description | Gene Sequence |
|---|---|---|
| 35 | I-E$^k$α-TCRα fusion | aataagcttctcgagcgccaccATGGCCACAATTGGAGCCCTGCTGTT AAGATTTTTCTTCATTGCTGTTCTGATGAGCTCCCAGAAGTCATGGGC TATCAAAGAGGAACACACCATCATCCAGGCGGAGTTCTATCTTTTACC AGACAAACGTGGAGAGTTTATGTTTGACTTTGACGGCGATGAGATTTT CCATGTAGACATTGAAAAGTCAGAGACCATCTGGAGACTTGAAGAATT TGCAAAGTTTGCCAGCTTTGAGGCTCAGGGTGCACTGGCTAATATAGC TGTGGACAAAGCTAACCTGGATGTCATGAAAGAGCGTTCCAACAACAC TCCAGATGCCAACGTGGCCCCAGAGGTGACTGTACTCTCCAGAAGCCC TGTGAACCTGGGAGAGCCCAACATCCTCATCTGTTTCATTGACAAGTT CTCCCCTCCAGTGGTCAATGTCACCTGGTTCCGGAATGGACGGCCTGT CACCGAAGGCGTGTCAGAGACAGTGTTTCTCCCGAGGGACGATCACCT CTTCCGCAAATTCCACTATCTGACCTTCCTGCCCTCCACAGATGATTT CTATGACTGTGAGGTGGATCACTGGGGTTTGGAGGAGCCTCTGCGGAA GCACTGGGAGTTTGAAGAGAAACCCTCCTCCCAGAAACTAAAGAGtg tgatgtcacgttgaccgagaaaaGCTTTGAAACAGATATgaacctaaa cttcaaaaccctgtcaGTTATGGGACTCCGAATCCtcctgctgaaagt agcgggatttaacCTGCTCATGACGCTgaggctgtggtccagttgagg atccgcta |
| 36 | MCC:I-E$^k$β-TCRβ fusion | aatCTCGAGCGCCACCATGGTGTGGCTCCCCAGAGTTCCCTGTGTGGC AGCTGTGATCCTGTTGCTGACAGTGCTGAGCCCTCCAGTGGCTTTGGT CAGAGACTCCGGATCCGCCAACGAGAGGGCCGACCTGATCGCCTACCT GAAGCAGGCCACCAAGGAATTCAGATCCGGAGGCGGAGGCTCCCTGGT GCCTCGGGGCTCCGGAGGCGGAGGCTCCGTCGACAGACCATGGTTTTT GGAATACTGTAAATCTGAGTGTCATTTCTACAACGGGACGCAGCGCGT GCGGCTTCTGGTAAGATACTTCTACAACCTGGAGGAGAACCTGCGCTT CGACAGCGACGTGGGCGAGTTCCGCGCGGTGACCGAGCTGGGGCGGCC AGACGCCGAGAACTGGAACAGCCAGCCGGAGTTCCTGGAGCAAAAGCG GGCCGAGGTGGACACGGTGTGCAGACACAACTATGAGATCTTCGATAA CTTCCTTGTGCCGCGGAGAGTTGAGCCTACGGTGACTGTGTACCCCAC AAAGACGCAGCCCCTGGAACACCACAACCTCCTGGTCTGCTCTGTGAG TGACTTCTACCCTGGCAACATTGAAGTCAGATGGTTCCGGAATGGCAA GGAGGAGAAAACAGGAATTGTGTCCACGGGCCTGGTCCGAAATGGAGA CTGGACCTTCCAGACACTGGTGATGCTGGAGACGGTTCCTCAGAGTGG AGAGGTTTACACCTGCCAGGTGGAGCATCCCAGCCTGACCGACCCTGT CACGGTCGAGTGGAAAGCACAGTCCACATCTGCACAGAACAAGtgtgg aatcactagtgcatcctatcatcaggggttctgtctgcaaccatcct atgagatcctactggggaaggccaccctatatgctgtgctggtcagtg gcctagtgctgatgGCCATGGTCAAGAAAAAAAATTCCgcggccgcat gatgagatctgagctccatagaggcg |
| 37 | HB:I-E$^k$β-TCRβ fusion | aatCTCGAGCGCCACCATGGTGTGGCTCCCCAGAGTTCCCTGTGTGGC AGCTGTGATCCTGTTGCTGACAGTGCTGAGCCCTCCAGTGGCTTTGGT CAGAGACTCCGGATCCGGCAAGAAGGTGATCACCGCCTTCAACGAGGG CCTGAAGGAATTCAGATCCGGAGGCGGAGGCTCCCTGGTGCCTCGGGG CTCCGGAGGCGGAGGCTCCGTCGACAGACCATGGTTTTTGGAATACTG TAAATCTGAGTGTCATTTCTACAACGGGACGCAGCGCGTGCGGCTTCT GGTAAGATACTTCTACAACCTGGAGGAGAACCTGCGCTTCGACAGCGA CGTGGGCGAGTTCCGCGCGGTGACCGAGCTGGGGCGGCCAGACGCCGA GAACTGGAACAGCCAGCCGGAGTTCCTGGAGCAAAAGCGGGCCGAGGT |

TABLE 4-continued

Examples of DNA sequences for encoding the proteins in Table 3.

| SEQ ID NO. | Description | Gene Sequence |
|---|---|---|
| | | GGACACGGTGTGCAGACACAACTATGAGATCTTCGATAACTTCCTTGT GCCGCGGAGAGTTGAGCCTACGGTGACTGTGTACCCCACAAAGACGCA GCCCCTGGAACACCACAACCTCCTGGTCTGCTCTGTGAGTGACTTCTA CCCTGGCAACATTGAAGTCAGATGGTTCCGGAATGGCAAGGAGGAGAA AACAGGAATTGTGTCCACGGGCCTGGTCCGAAATGGAGACTGGACCTT CCAGACACTGGTGATGCTGGAGACGGTTCCTCAGAGTGGAGAGGTTTA CACCTGCCAGGTGGAGCATCCCAGCCTGACCGACCCTGTCACGGTCGA GTGGAAAGCACAGTCCACATCTGCACAGAACAAGtgtggaatcactag tgcatcctatcatcagggggttctgtctgcaaccatcctctatgagat cctatggggaaggccaccctatatgctgtgctggtcagtggcctagtg ctgatgGCCATGGTCAAGAAAAAAAATTCCgcggccgcatgatgagat ctgagctccatagaggcg |
| 38 | CD80-Lck (mCD80-mLck fusion) | acgtctagatacctcgaggccaccATGGCTTGCAATTGTCAGttgatg caggatacaccactcctcaagtttccatgtccaaggctcattcttctc tttgtgctgctgattcgtctttcacaagtgtcttcagatgttgatgaa caactgtccaagtcagtgaaagataaggtattgctgccttgccgttac aactctcctcatgaagatgagtctgaagaccgaatctactggcaaaaa catgacaaagtggtgctgtctgtcattgatgggaaactaaaagtgtgg cccgagtataagaaccggactttatatgacaacactacctactctctt atcatcctgggcctggtcctttcagaccggggcacatacagctgtgtc gttcaaaagaaggaaagaggaacgtatgaagttaaaaacttggcttta gtaaagttgtccatcaaagctgacttctctaccccaacataactgag tctggaaacccatctgcagacactaaaaggattacctgctttgcttcc ggggggtttcccaaagcctcgcttctcttggtggaaaatggaagagaat tacctggcatcaatacgacaatttcccaggatcctgaatctgaattgt acaccattagtagccaactagatttcaatacgactcgcaaccacacca ttaagtgtctcattaaatatggagatgctcacgtgtcagaggacttca cctgggaaaaaccccagaagaccctcctgatagcaagaacacacttg tgctctttggggcaggattcggcgcagtaataacagtcgtcgtcatcg ttgtcatcatcaaatgcttctgtaagcacagaagctgtttcagaagaa atgaggcaagcagagaaacaaacaacagcct tacct tcgggcctgaag aagcattagctGAACAGACCGTCTTCCTTaccactagtCACTATCCCA TAGTCccactggacagcaagatctcgctgcccatccggaattggctct gaagtgcgggacccactggtcacctatgagggatactcccaccagcat ccccgctgcaagacaacctggttatcgccctgcacagttatgagccct cccatgatggagacttgggctttgagaagggtgaacagctccgaatcc tggagcagagcggtgagtggtggaaggctcagtccctgacgactggcc aagaaggattcattcccttcaacttcgtggcgaaagcaaacagcctgg agcctgaaccttggttcttcaagaatctgagccgtaaggacgccgagc ggcagcttttggcgcccgggaacacgcatggatccttcctgatccggg aaagcgaaagcactgcggggtcctttttccctgtcggtcagagacttcg accagaaccagggagaagtggtgaaacattacaagatccgtaacctag acaacggtggcttctacatctcccctcgtatcacttttccggattgc acgatctagtccgccattacaccaacgcctctgatgggctgtgcacaa agttgagccgtccttgccagacccagaagccccagaaaccatggtggg aggacgaatgggaagttcccagggaaacactgaagttggtggagcggc tgggagctggccagttcggggaagtgtggatggggtactacaacggac acacgaaggtggcggtgaagagtctgaaacaagggagcatgtcacccg acgccttcctggctgaggctaacctcatgaagcagctgcagcacccgc ggctagtccggctttatgcagtggtcacccaggaacccatctacatca tcacggaatacatggagaacgggagcctagtagattttctcaagactc cctcgggcatcaagagaatgtcaacaaacttttggacatggcagccca gattgcagagggcatggcgttcatcgaagaacagaattacatccatcg ggacctgcgcgccgccaacatcaggtgtctgacacgctgagagcaaga ttgcagactttggcctggcgcgcctcattgaggacaatgagtacaccc ccgggagggggccaaattccccattaagtggacagcaccagaagccat taactatggaccttcaccatcaagtcagacgtgtggtccttcgggatc ttgcttacagagatcgtcacccacggtcgaatcccttacccaggaatg accaaccctgaagtcattcagaacctggagagaggctaccgcatggtg agacctgacaactgtccggaagagctgtaccacctcatgatgctgtgc tggaaggagcgccagaggaccggcccacgtttgactaccttcggagt gttctggatgacttcttcacagccacagagggcCAGTACCAGCCCCAG CCTggtacctagtgagaattctacatg |
| 39 | CD86-Lck (mCD86-mLck fusion) | tactctagatacctcgaggccaccATGGACCCCAGATGCACCatgggc ttggcaatcctttatctttgtgacagtcttgctgatctcagatgctgtt tccgtggagacgcaagcttatttcaatgggactgcatatctgccgtgc ccatttacaaaggctcaaaacataagcctgagtgagctggtagtattt tggcaggaccagcaaaagttggttctgtacgagcactatttgggcaca gagaaacttgatagtgtgaatgccaagtacctgggccgcacgagcttt gacaggaacaactggactctacgacttcacaatgttcagatcaaggac atgggctcgtatgattgttttatacaaaaaaagccacccacaggatca attatcctccaacagacattaacagaactgtcagtgatcgccaacttc |

TABLE 4-continued

Examples of DNA sequences for encoding the proteins in Table 3.

| SEQ ID NO. | Description | Gene Sequence |
|---|---|---|
| | | agtgaacctgaaataaaactggctcagaatgtaacaggaaattctggc<br>ataaatttgacctgcacgtctaagcaaggtcacccgaaacctaagaag<br>atgtattttctgataactaattcaactaatgagtatggtgataacatg<br>cagatatcacaagataatgtcacagaactgttcagtatctccaacagc<br>ctctctctttcattcccggatggtgtgtggcatatgaccgttgtgtgt<br>gttctggaaacggagtcaatgaagatttcctccaaaccttctcaattt<br>cactcaagagtttccatctcctcaaacgtattggaaggagattacagc<br>ttcagttactgtggccctcctccttgtgatgctgctcatcattgtatg<br>tcacaagaagccgaatcagcctagcaggcccagcaacacagcctctaa<br>gttagagcgggatagtaacgctgacagagagactatcaacctgaagga<br>acttgaacccaaattgcttcagcaaaaccaaatgcagagtgtactag<br>tCACTATCCCATAGTCccactggacagcaagatctcgctgcccatccg<br>gaatggctctgaagtgcgggacccactggtcacctatgagggatctct<br>cccaccagcatcccgctgcaagacaacctggttatcgccctgcacag<br>ttatgagccctcccatgatggagacttgggctttgagaagggagaaca<br>gctccgaatcctggagcagagcggtgagtggtggaaggctcagtccct<br>gacgactggccaagaaggcttcattcccttcsacttcgtggcgaaagc<br>aaacagcctggagcctgaaccttggttcttcaagaatctgagccgtaa<br>ggacgccgagcggcagcttttggcgcccgggaacacgcatggatcctt<br>cctgatccgggaaagcgaaagcactgcggggtccttttccctgtcggt<br>cagagacttcgaccagaaccagggagaagtggtgaaacattacaagat<br>ccgtaacctagacaacggtggcttctacatctcccctcgtatcactt<br>tcccggattgcacgatctagtccgccattacaccaacgcctctgatgg<br>gctgtgcacaaagttgagccgtccttgccagacccagaagccccagaa<br>accatggtgggaggacgaatgggsagttcccagggaaacactgaagtt<br>ggtggagcggctgggagctggccagttcggggaagtgtggatgggta<br>ctacaacggacacacgaaggtggcggtgaagagtctgaaacaagggag<br>catgtcccccgacgccttcctggctgaggctaacctcatgaagcagct<br>gcagcacccgcggctagtccggctttatgcagtgggtcacccaggaac<br>ccatctacatcatcacggaatacatggagaacgggagcctagtagatt<br>ttctcaagactccctcgggcatcaagttgaatgtcaacaaactttttgg<br>acatggcagcccagattgcagagggcatggcgttcatcgaagaacaga<br>attacatccatcgggacctgcgcgccgccaacatcctggtgtctgaca<br>cgctgagctgcaagattgcagactttggcctggcgcgcctcattgagg<br>acaatgagtacacggcccgggaggggggccaaatttcccattaagtgga<br>cagcaccagaagccattaactatgggaccttcaccatcaagtcagacg<br>tgtggtccttcgggatcttgcttacagagatcgtcacccacggtcgaa<br>tcccttacccaggaatgaccaaccctgaagtcattcagaacctggaga<br>gaggctaccgcatggtgagacctgacaactgtccggaagagctgtacc<br>acctcatgatgctgtgctggaaggagcgcccagaggaccggcccacgt<br>ttgactaccttcggagtgttctggatgacttcttcacagccacagagg<br>gcCAGTACCAGCCCCAGCCTggtacctagtgagaattctacatg |

The disclosures of the following U.S. Patents are incorporated in their entirety by reference herein: U.S. Pat. Application No. 20140219975; U.S. Pat. Nos. 8,450,112; 7,741,465; 6,319,494; CA 2209300; CA 2104957; EP 0574512; U.S. Pat. Nos. 6,407,221; 6,268,411; U.S. Pat. Application No. 20040258697; EP 1292621; EP 2659893; WO 2011101681; WO 2005054292; EP 1379670; U.S. Pat. Nos. 6,056,952; 6,410,319; 8,524,234; 7,871,817.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A chimeric receptor (MHCR) comprising (i) a class I major histocompatibility complex (MHC) portion, comprised of at least a portion of an extracellular domain of a class I MHC protein, beta2-microglobulin and a targeted peptide, directly fused in the absence of a linker, to a T cell receptor (TCR) portion, comprised of at least an extracellular domain of a TCR, a transmembrane domain of a TCR and at least a portion of a cytoplasmic domain of a TCR protein, wherein the MHCR binds to a TCR of a target cell through the targeted peptide of the MHC portion of the MHCR, or (ii) a class II major histocompatibility complex (MHC) portion, comprised of at least a portion of an extracellular domain of a class II MHC protein and a targeted peptide, directly fused in the absence of a linker, to a T cell receptor (TCR) portion, comprised of at least an extracellular domain of a TCR, a transmembrane domain and at least a portion of a cytoplasmic domain of a TCR protein, wherein the MHCR binds to a TCR of a target cell through the targeted peptide of the MHC portion of the MHCR.

2. The MHCR of claim 1, wherein binding of the MHCR to the TCR of the target cell initiates a signaling cascade effective for eliminating the target cell.

3. The MHCR of claim 1, wherein the MHC protein, the TCR protein, or both the MHC protein and the TCR protein are mammalian proteins.

4. The MHCR of claim 1, wherein the targeted peptide is integrated into the MHC portion, or directly or indirectly fused to the MHC portion.

5. The MHCR of claim 1, wherein the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment thereof, or a combination thereof.

6. The MHCR of claim 1, wherein the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment that is at least 90% identical to HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, or H2-EK beta, a fragment thereof, or a combination thereof.

7. The MHCR of claim 1, wherein the TCR protein comprises TRAC, TRBC1, TRBC2, TRDC, TRGC1, TRGC2, TCRA, TCB1, TCB2, TCC1, TCC2, TCC3, TCC4, a fragment thereof, or a combination thereof.

8. The MHCR of claim 1, wherein the TCR protein comprises TRAC, TRBC1, TRBC2, TRDC, TRGC1, TRGC2, TCRA, TCB1, TCB2, TCC1, TCC2, TCC3, TCC4, a fragment that is at least 90% identical to TRAC, TRBC1, TRBC2, TRDC, TRGC1, TRGC2, TCRA, TCB1, TCB2, TCC1, TCC2, TCC3, or TCC4, a fragment thereof, or a combination thereof.

9. The MHCR of claim 1, wherein the MHCR complexes with a CD3 subunit.

10. The MHCR of claim 1, wherein binding of the MHCR to the TCR of the target cell instructs the target cell to differentiate to a specific effector function.

* * * * *